(12) United States Patent
Nakamura et al.

(10) Patent No.: US 7,033,475 B2
(45) Date of Patent: Apr. 25, 2006

(54) ELECTROPHORETIC APPARATUS

(75) Inventors: Shin Nakamura, Shiga (JP); Toru Kaji, Kyoto (JP); Rintaro Yamamoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 450 days.

(21) Appl. No.: 09/982,964

(22) Filed: Oct. 22, 2001

(65) Prior Publication Data

US 2002/0046949 A1    Apr. 25, 2002

(30) Foreign Application Priority Data

| Oct. 25, 2000 | (JP) | ............................. 2000-325049 |
| Oct. 25, 2000 | (JP) | ............................. 2000-325104 |
| Dec. 25, 2000 | (JP) | ............................. 2000-393381 |
| Apr. 13, 2001 | (JP) | ............................. 2001-115014 |

(51) Int. Cl.
*G01N 27/447* (2006.01)
*G01N 27/26* (2006.01)

(52) U.S. Cl. ..................................... 204/603; 204/452

(58) Field of Classification Search ........ 204/451–455, 204/601–605
See application file for complete search history.

(56) References Cited

U.S. PATENT DOCUMENTS

| 4,911,807 | A | * | 3/1990 | Burd ............................ 204/453 |
| 5,038,021 | A | * | 8/1991 | Uchigaki et al. ............ 235/375 |
| 5,137,609 | A | * | 8/1992 | Manian et al. ............... 204/452 |
| 5,483,075 | A | * | 1/1996 | Smith et al. .............. 250/458.1 |
| 5,627,643 | A | * | 5/1997 | Birnbaum et al. ........... 356/344 |
| 5,667,656 | A | * | 9/1997 | Kambara ...................... 204/603 |
| 5,759,369 | A | * | 6/1998 | Menchen et al. ............ 204/458 |
| 5,872,010 | A | | 2/1999 | Karger et al. |
| 5,954,931 | A | * | 9/1999 | Maracas et al. ............. 204/451 |
| 5,958,202 | A | * | 9/1999 | Regnier et al. .............. 204/451 |
| 6,042,708 | A | * | 3/2000 | Nakanishi et al. ........... 204/452 |
| 6,126,804 | A | * | 10/2000 | Andresen ..................... 204/601 |
| 6,132,579 | A | * | 10/2000 | Edwards et al. ............. 204/451 |
| 6,207,031 | B1 | * | 3/2001 | Adourian et al. ............ 204/451 |
| 6,465,257 | B1 | * | 10/2002 | Parce et al. .................. 436/180 |

FOREIGN PATENT DOCUMENTS

| EP | 934771 A1 * | 8/1999 |
| EP | 1 006 355 | 6/2000 |

(Continued)

OTHER PUBLICATIONS

Yining Shi et al, Anal. Chem. Dec. 1999, 71, 5354-5361.*

(Continued)

*Primary Examiner*—Nam Nguyen
*Assistant Examiner*—Jeffrey T. Barton
(74) *Attorney, Agent, or Firm*—Westerman, Hattori, Daniels & Adrian, LLP

(57) ABSTRACT

An electrophoretic apparatus which can analyze multiple tests specimens and being comprised of an electrophoretic member having a relatively simple configuration of passages, such that one or a plurality of passages are formed inside a plate-shaped member therein in which holes are formed connecting to the passages at positions corresponding to the ends of each passage, a voltage application part for applying a voltage across the passages, a detector part for detecting a specimen within the passage and an electrophoretic-member holding part for holding a plurality of the electrophoretic members so as to provide for simultaneous electrophoretic operations.

6 Claims, 14 Drawing Sheets

FOREIGN PATENT DOCUMENTS

| | | | |
|---|---|---|---|
| JP | 61-213974 | | 9/1986 |
| JP | 09-243598 | | 9/1997 |
| JP | 10-73568 | | 3/1998 |
| JP | 10132783 A | * | 5/1998 |
| JP | 10-148628 | | 6/1998 |
| JP | 10-206384 | | 8/1998 |
| JP | 10-246721 | | 9/1998 |
| JP | 11-311616 | | 11/1999 |
| JP | 2000-074835 | | 3/2000 |
| JP | 2000227414 A | * | 8/2000 |
| JP | 2000283960 A | * | 10/2000 |
| WO | WO 00/02038 | | 1/2000 |

OTHER PUBLICATIONS

D. Harrison et al., "*Rapid separation of fluorescein derivatives using a micromachined capillary electrophoresis system*", Analytica Chemica Acta, 283, (1993) pp. 361-366. Month N/A.

Y. Shi et al., "*Radial Capillary Array Electrophoresis Microplate and Scanner for High-Performance Nucleic Acid Analysis*", Analytical Chemistry, vol. 71, No. 23, Dec. 1999, pp. 5354-5361.

* cited by examiner

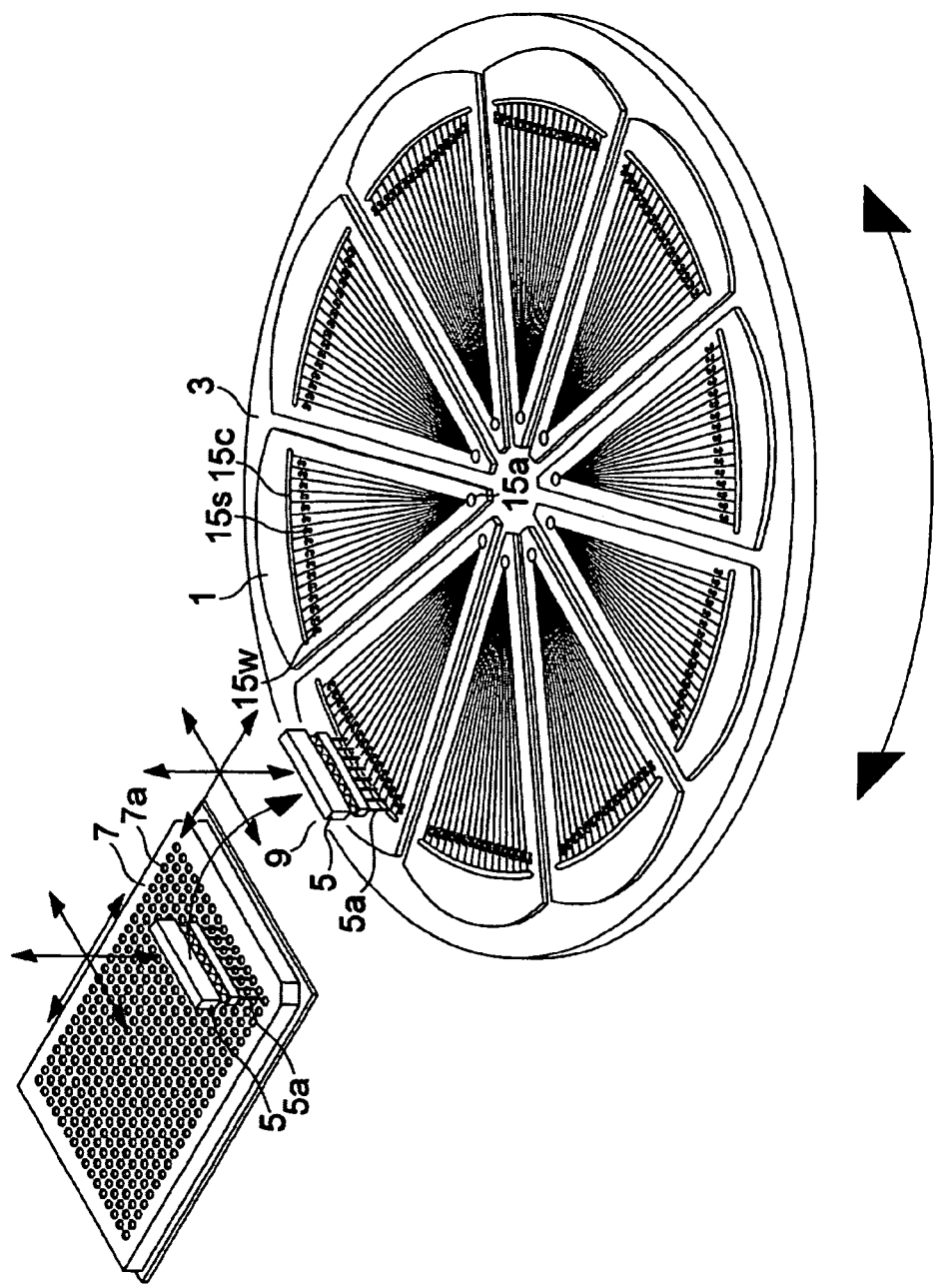

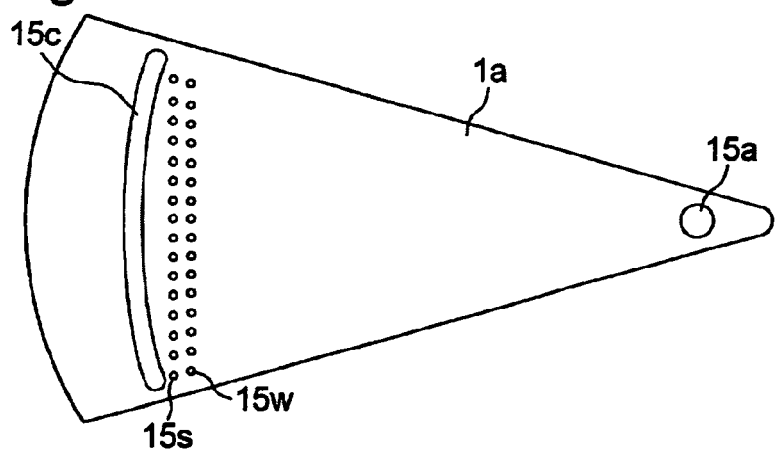
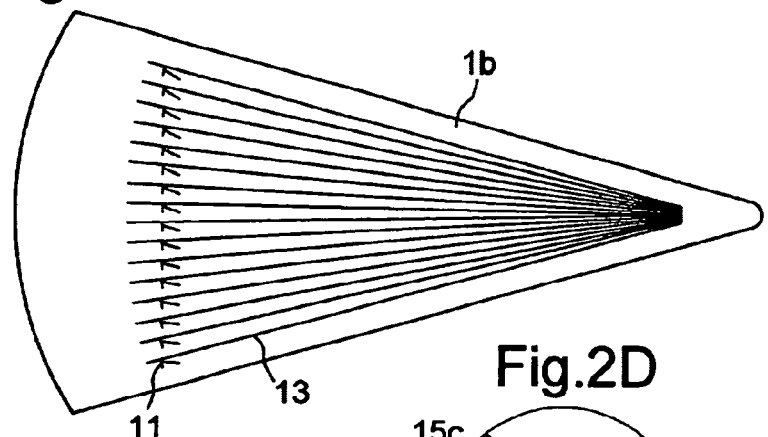
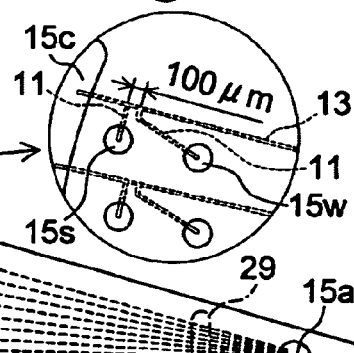
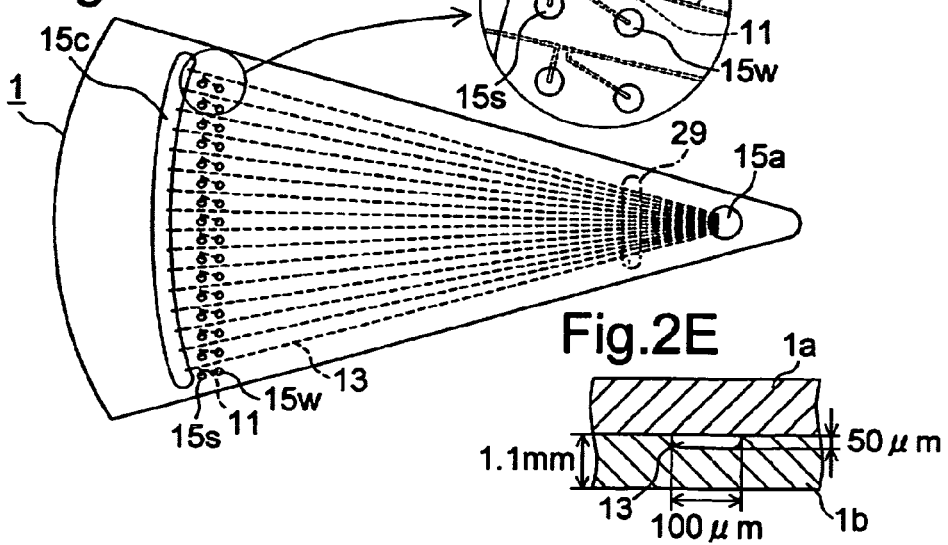
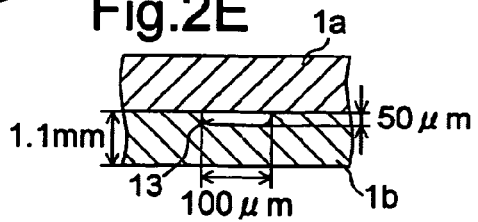

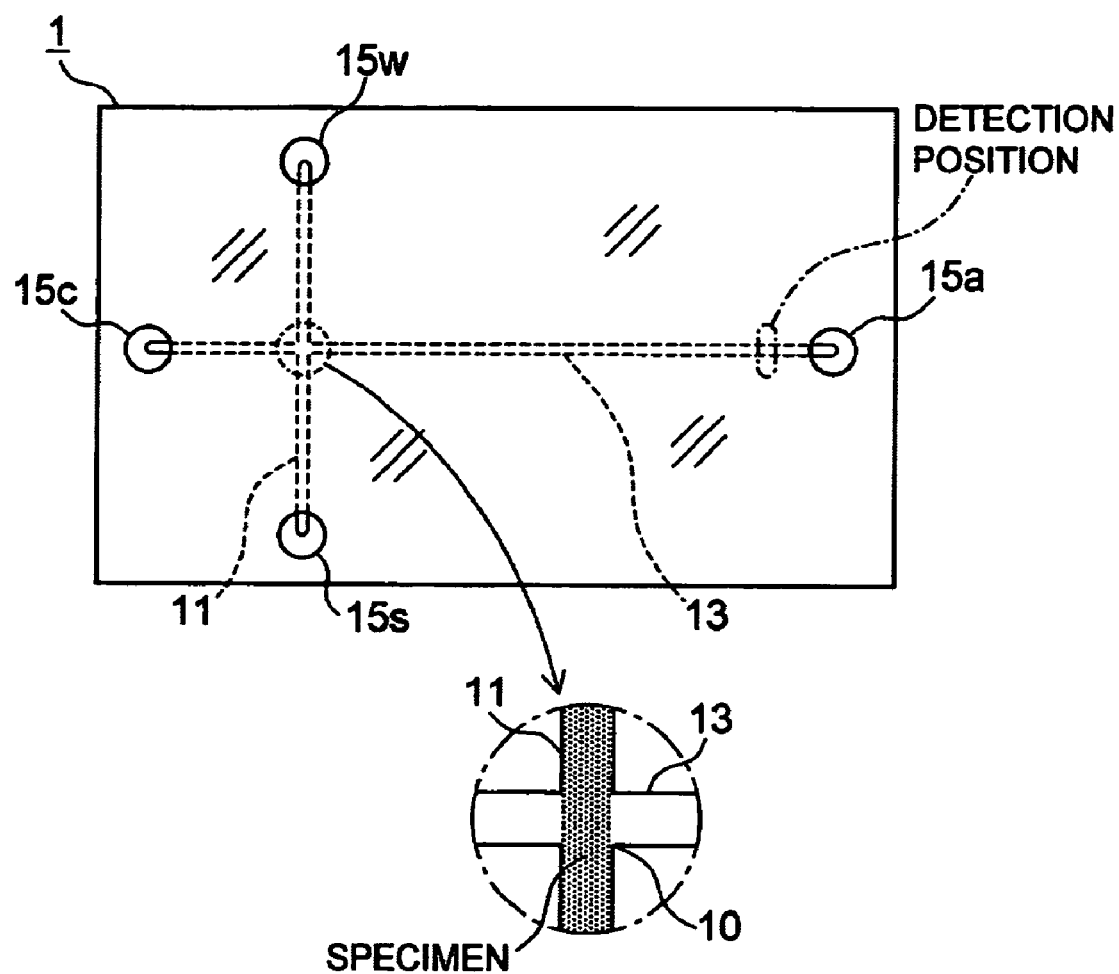

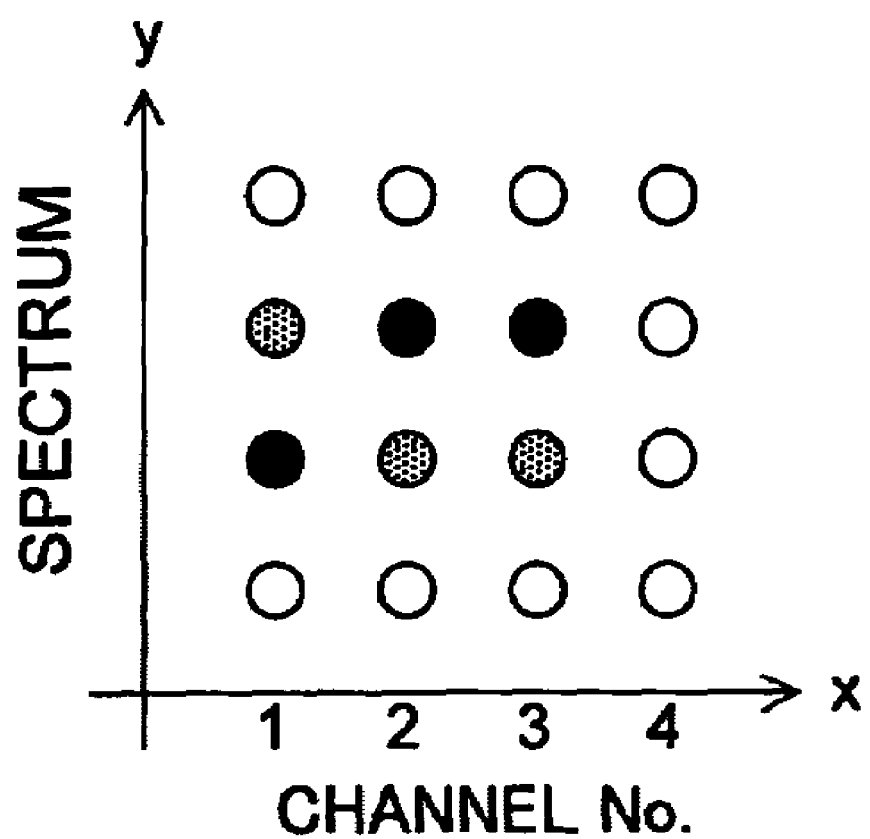

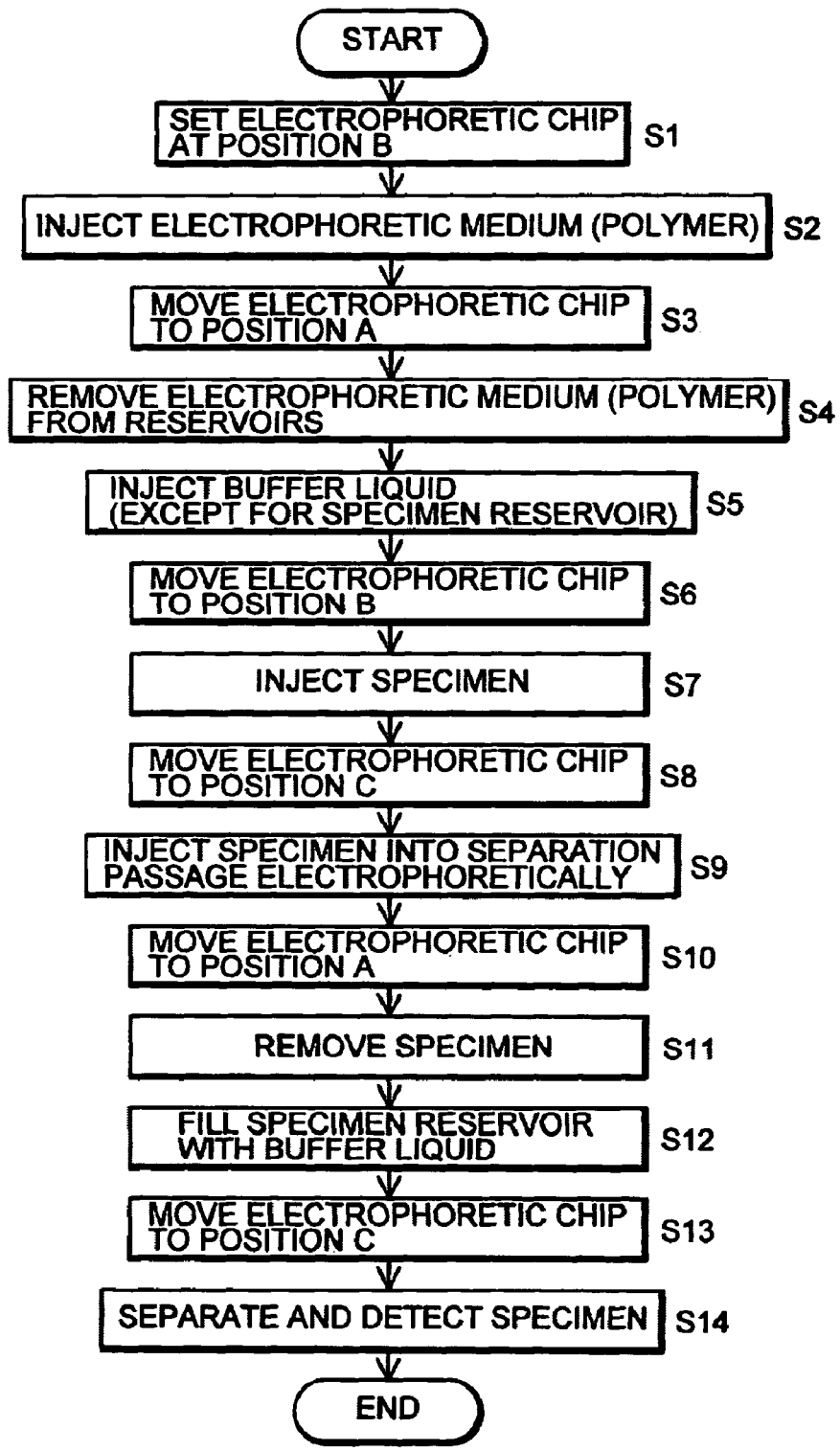

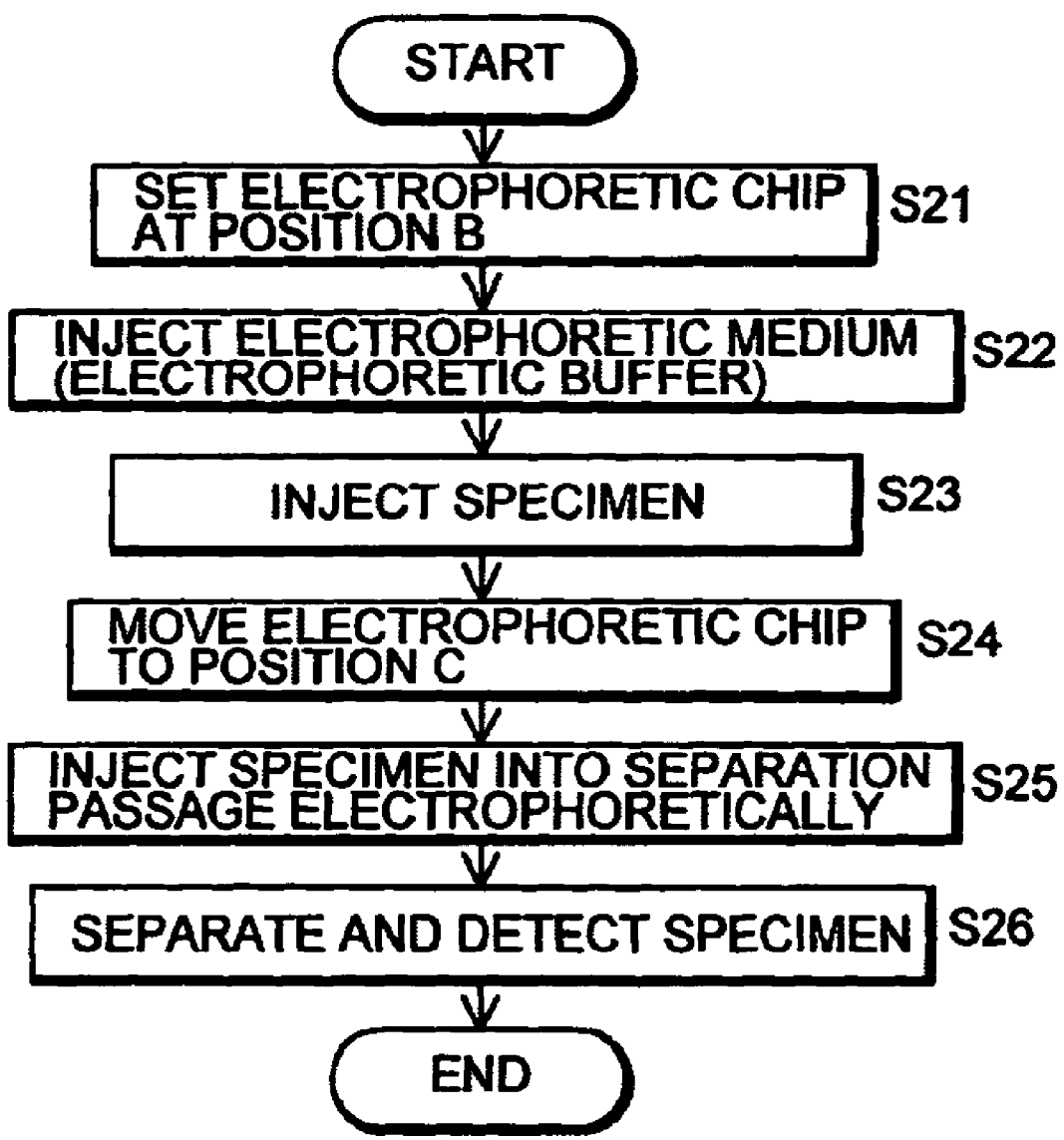

ELECTROPHORETIC APPARATUS

BACKGROUND OF THE INVENTION

1. Field of the Invention

The invention relates to an electrophoretic apparatus for analyzing a small amount of protein, nucleic acid, drugs, and the like, and more particularly to an electrophoretic apparatus using an electrophoretic member having a plate-shaped member in which is formed one or a plurality of passages through which a specimen migrates electrophoretically.

2. Description of the Related Art

Conventionally, an electrophoretic apparatus has been used to analyze an extremely small amount of protein, nucleic acid or the like, represented by a capillary electrophoretic apparatus. In the capillary electrophoretic apparatus, a glass-made capillary (hereinafter called capillary also) with an inner diameter of 100 μm or less is filled with an electrophoretic medium and then has a specimen introduced at one end thereof and has its both ends wetted with a buffer liquid, through which is applied a high voltage between the two ends in order to develop an analysis-subject substance in the capillary. The capillary has a large surface area as compared to its volume, that is, has a high cooling efficiency, so that a high voltage can be applied on it, thus qualifying it for use in analysis of an extremely small amount of a specimen such as DNA (deoxyribo-nucleic acid) at a high speed and a high resolution.

The capillary has a small outer diameter of about 100–500 μm and is easily broken, thus having a problem that the user finds it difficult to replace it Also, sometimes it may have insufficient heat radiation, which has an adverse effect on a separated state. Furthermore, since a voltage is applied between the ends of the capillary through a buffer liquid, it needs to have at least an extra length required for wetting with the buffer solution, thus bringing about a problem that it must have a certain design length.

To guard against this, there has been proposed such an aspect replacing a capillary that may be improved in analysis speed and apparatus size, disclosed in an item of D. J. Harrison et al./Anal. Chem. 1993, 283, 361–366, which describes an electrophoretic member (hereinafter called electrophoretic chip also) which is formed by connecting two substrates. An example of the electrophoretic chip is shown in FIG. 14.

An electrophoretic chip 221 is comprised of one pair of substrates 221a and 221b made of a transparent plate-shaped inorganic material (e.g. glass, quartz, silicon or the like) or plastic in such a configuration that, using a photolithographic technology used in manufacturing of semiconductor devices or a micro-machining technology, mutually intersecting electrophoretic capillary channels 223 and 225 are formed in one substrate 221b and, in the other substrate 221a, through-holes are formed as an anode reservoir 227a, a cathode reservoir 227c, a specimen reservoir 227s, and a waste reservoir 227w at positions corresponding to the ends of these channels 223 and 225. The electrophoretic chip 221 is used in such a state as shown in FIG. 14C, where the substrates 221a and 221b are connected on one another. Such an electrophoretic chip has thus two channels as formed to intersect with each other and, therefore, is also called a cross-channel type electrophoretic chip.

When using this electrophoretic chip 221 for electrophoresis, prior to analysis, an electrophoretic medium is delivered under pressure by, for example, a syringe to fill the channels 223 and 225 and the reservoirs 227a, 227c, 227s, and 227w from, for example, the anode reservoir 227a. Subsequently, the electrophoretic medium injected in the reservoirs 227a, 227c, 227s, and 227w is removed to then inject a specimen into the specimen reservoir 227s corresponding to one end of the shorter channel (specimen injection passage) 223 and a buffer solution into the other specimen reservoirs 227a, 227c, and 227w.

The electrophoretic chip 221 filled with the electrophoretic medium, the specimen, and the buffer liquid is mounted to an electrophoretic apparatus. Predetermined voltages are applied on the reservoirs 227a, 227c, 227s, and 227w to cause the specimen to electrophoretically migrate through the passage 223 up to an intersection 229 of the passages 223 and 225. The voltages applied on the reservoirs 227a, 227c, 227s, and 227w are switched so that a voltage applied between the reservoirs 227a and 227c at the ends of the longer channel (separation passage) 225 may cause the specimen present at the intersection 229 to be injected into the passage 225. After this injection, the specimen contained in the reservoir 227s is replaced by the buffer liquid. After that, electrophoretic voltages are applied on the reservoirs 227a, 227c, 227s, and 227w to separate the specimen thus injected into the passage 225 in this passage 225. A detector, disposed at a proper position along the passage 225, is used to detect a specimen thus separated by electrophoresis. It is specifically detected using a absorptiometric, fluoro-metric, electrochemical, or electric-conductivity method.

Also, such analysis conditions as a design of the passages in the electrophoretic chip or a composition of the electrophoretic medium depend on use and specimens. An electrophoretic chip having a different design of the passages is described in, for example, a repot of Yining Shi et al./Anal. Chem. 1999, 71, 5354–5361, in which the electrophoretic chip is provided with many separation passages formed therein in a radial manner.

Also, such an electrophoretic chip is available that has straight channels having no intersection therebetween.

An electrophoretic apparatus using in analysis such an electrophoretic chip that has only one separation passage as shown in FIG. 14 has a poor analysis efficiency, thus suffering from a problem that it is not suitable for simultaneous analysis, which is desired recently, of multiple test-specimens.

SUMMARY OF THE INVENTION

It is the first object of the invention to provide an electrophoretic apparatus which can analyze multiple test-specimens even with such an electrophoretic member that has a simple configuration of passages.

In order to attain the first object, one aspect of an electrophoretic apparatus of the invention uses an electrophoretic member in which one or a plurality of passages are formed inside a plate-shaped member of which holes are formed reaching these passages at positions corresponding to the ends of each of these passages and includes a voltage application part for applying a voltage across the passages in the electrophoretic member, a detector part for detecting a specimen present in the passages in the electrophoretic member, and an electrophoretic-member holding part for holding a plurality of electrophoretic members engaged in simultaneous electrophoretic operations.

The electrophoretic apparatus of the aspect can use a plurality of electrophoretic members disposed on an electrophoretic-member holding part, to conduct electrophoretic analysis on multiple test-specimens at a time.

Since the invention can thus reduce the number of separation passages per electrophoretic chip in electrophoretic analysis on multiple test-specimens, the electrophoretic chips can be manufactured more easily to thereby improve the yield, thus reducing the analysis costs.

To conduct simultaneous analysis on multiple test-specimens employing different effective electrophoretic lengths of the separation passages, a prior art electrophoretic apparatus needs to prepare one electrophoretic member provided with such a plurality of separation passages with different effective electrophoretic lengths and so conventionally finds it difficult to conduct such an analysis on multiple test-specimens under the condition of multiple effective electrophoretic lengths. In contrast, the electrophoretic apparatus of the invention, which uses a plurality of electrophoretic members, can prepare a plurality of kinds of electrophoretic members with different effective electrophoretic lengths to then select one of them that has an appropriate effective electrophoretic length and dispose it on the electrophoretic-member holding part beforehand, thus conducting simultaneous analysis on multiple test-specimens under the condition of multiple effective electrophoretic lengths.

It is the second object of the invention to provide a detecting device to realize a high S/N ratio of a detection signal.

In order to attain the second object, another aspect of an electrophoretic apparatus of the invention has a detecting part consists of a fluorescent-light detecting device for detecting a fluorescent light in a detection range, the fluorescent-light detecting device comprising a first optical system for focusing, for image formation, a light from the detecting range into a slit hole; and a second optical system provided with a reflection-type diffraction grating, for separating a light from the slit hole and focusing the light, for image formation, onto a detecting element.

It is the third object of the invention to provide a system to enable an electrophoretic apparatus to operate automatically.

In order to attain the third object, further aspect of an electrophoretic apparatus of the invention has an electrophoretic-medium filling mechanism for filling an electrophoretic medium into the passages and the reservoirs through the reservoirs of the electrophoretic member and a specimen injection mechanism for injecting a specimen into one of the reservoirs; and a control part for controlling the electrophoretic apparatus including the mechanisms so that they all may operate automatically.

In recent years, such electrophoretic chips are used that have a large chip size or provided with a plurality of channels or even such straight channels that have no intersection between the channels. These chips all fall in the category of the electrophoretic member of the invention.

The term "passage" in the present invention includes not only such channels as shown in the examples but also various channels such as a capillary and a closed channel.

BRIEF DESCRIPTION OF THE DRAWINGS

FIG. 1 is a perspective view for showing one embodiment of the invention;

FIGS. 2A–2E are illustrations for showing one example of an electrophoretic chip in which the many separation passages are formed and which are mounted to the embodiment shown in FIG. 1, of which FIG. 2A is a top view for showing one substrate, FIG. 2B is a top view for showing the other substrate, FIG. 2C is a top view for showing a state where both substrates are connected on one another, FIG. 2D is an expanded top view for showing a part encircled in FIG. 2C, and FIG. 2E is a cross-sectional view for showing a part of the separation passages of FIG. 2C;

FIG. 7 is a plan view for showing a simplified electrophoretic chip as well as an expanded illustration for showing an intersection between a specimen-injection passage and a separation passage when a specimen is introduced;

FIGS. 8A–8C are illustrations for showing an electrophoretic chip in which many separation passages are formed, of which FIG. 8A is a top view for showing one substrate, FIG. 8B is a top view for showing the other substrate, and FIG. 8C is a top view for showing a state where both substrates are connected on one another;

FIG. 9 is a graph for showing a detection signal where specimens, labeled with four kinds of fluorescent materials with different fluorescent wavelengths, are separated and detected using the electrophoretic chip of FIG. 8C;

FIG. 12 is a flowchart for showing an example of the operations of the embodiment of FIG. 11;

FIG. 13 is a flowchart for showing another example of the operations of the embodiment of FIG. 11; FIG. 14B is a top view for showing the other substrate, and FIG. 14C is a side view for showing a state where both substrates are connected one on the other.

DESCRIPTION OF THE PREFERRED EMBODIMENTS

Figure 3:
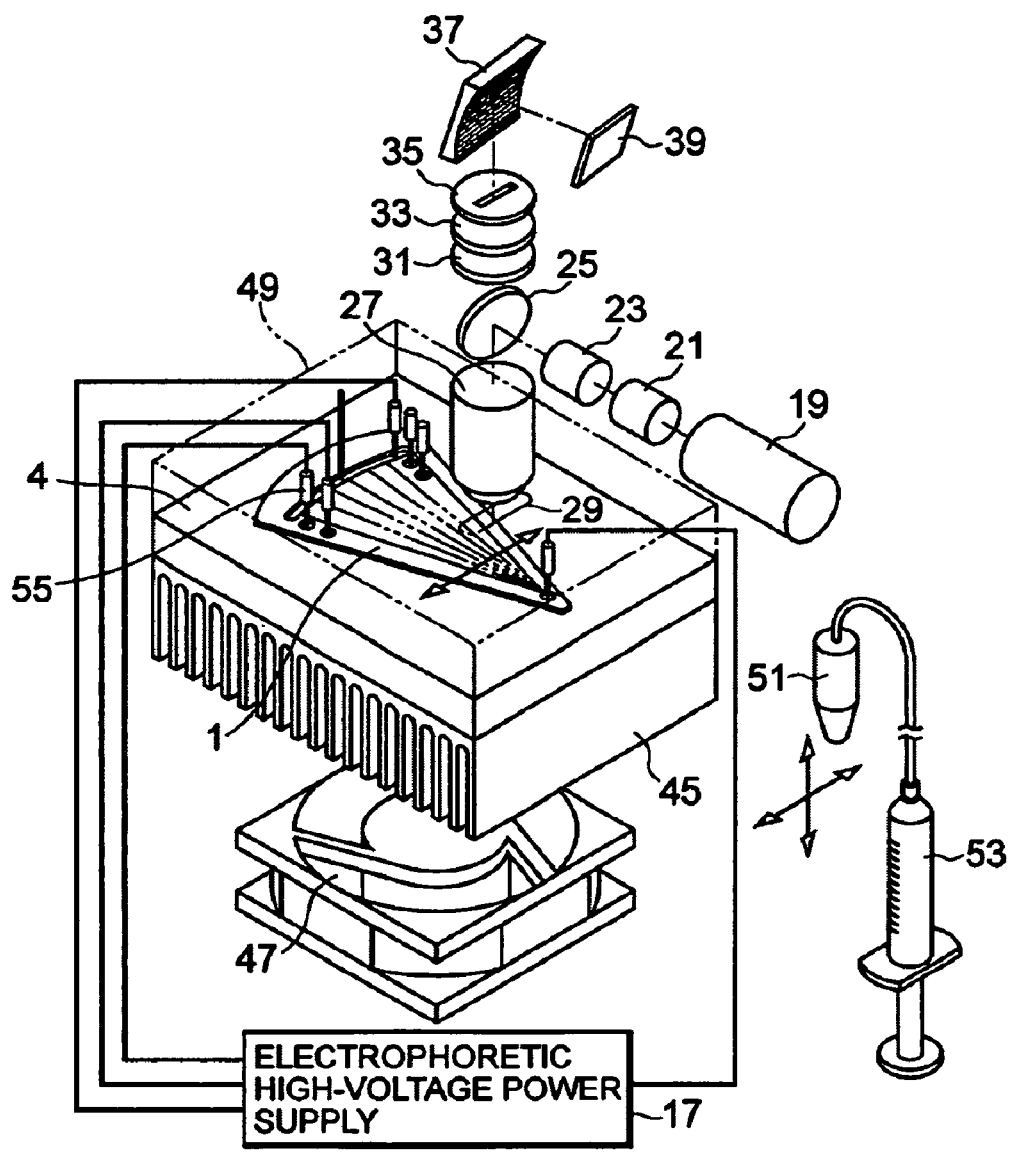
FIG. 3 is a partial perspective view for showing an embodiment of an electrophoretic apparatus provided with a preferred fluorescent-light detecting device.

FIG. 1 is a perspective view for showing one embodiment of the invention. FIGS. 2A–2E are illustrations for showing one example of an electrophoretic chip in which many separation passages are formed and which is mounted to the embodiment of FIG. 1, of which FIG. 2A is a top view for showing one substrate, FIG. 2B is a top view for showing the other substrate, FIG. 2C is a top view for showing a state where both substrates are connected on one another, FIG. 2D is an expanded top view for showing an encircled part of FIG. 2C, and FIG. 2E is a cross-sectional view for showing a separation passage part of FIG. 2C.

Firstly, the electrophoretic chip shown in FIGS. 2A–2E shall be described.

An electrophoretic chip 1 is comprised of one pair of plate-shaped substrates 1a and 1b made of an inorganic material (e.g., glass, quartz, silicon or the like) or plastic. The substrates 1a and 1b measure, for example, 1.1 mm in thickness.

One substrate 1b has 16 pairs, each of which consists of a specimen-introducing passage 11 and a separation passage 13 intersected with each other, formed in its surface by a photolithographic technology used in semiconductor-device manufacturing processes or by a micro-machining technology. The specimen-introducing passage 11 and the separation passage 13 measure approximately, for example, 100 µm in width and 50 µm in depth. Each of these 16 pairs of the passages 11 and 13 are arranged in a sector shape with, as a pivot thereof, one end side of the separation passage 13 opposite the side intersecting with the specimen-introducing passage 11 so that they do not intersect with the other pairs. The substrates 1a and 1b are formed in a sector shape so as to match the arrangement of the separation passage 13.

The other substrate 1a has an anode reservoir 15a, a cathode reservoir 15c, a specimen reservoir 15s, and a waste reservoir 15w formed as through holes therein at positions corresponding to the ends of the passages 11 and 13. The reservoirs 15s and 15w are provided for each pair of passages 11 and 13. The anode reservoir 15a is provided common to each one end side of the separation passage 13 of each pair on the pivot side in the sector-shape arrangement. The cathode reservoir 15c is formed in an elongated hole common to the other end side of the separation passage 13 of each pair.

As shown in FIG. 2D, the specimen-introducing passage 11 extending from the specimen reservoir 15s and the specimen-introducing passage 11 extending from the waste reservoir 15w are connected to the separation passage 13 with a spacing of, for example, 100 µm therebetween.

The electrophoretic chip 1 is used in a state where both substrates 1a and 1b are connected on one another.

Such an electrophoretic chip is called a multi-channel micro-chip because it has many separation passages formed therein.

The electrophoretic apparatus shall be described as follows with respect to FIG. 1.

A disk-shaped multi-chip turn table (electrophoretic-member holding part) 3 is provided. On the table 3 are held, for example, 10 sheets of the electrophoretic chips 1. These 10 electrophoretic chips 1 are evenly spaced in arrangement on the table 3 in such a manner that the substrate 1a in which are formed the reservoirs 15a, 15c, 15s, and 15w faces upward and also that the pivot of their sector shapes is oriented toward the center. This arrangement of the electrophoretic chips can be realized by, for example, forming in the surface of the table 3 a recess in correspondence with the sector shape of the electrophoretic chips 1 beforehand or by forming alignment holes in the electrophoretic chips 1 so that pins or any other protruding members may be arranged at position corresponding to those holes. The table 3 is provided with a mechanism (not shown) for rotating the table 3 using the center of the table 3 as a rotation axis in a place in which the electrophoretic chip 1 is held.

Near the table 3 is provided a specimen dispensing mechanism fitted with a specimen transfer head 5 and specimen plate 7 for containing many test-specimens at a time. In the figure, a part not constituting the head 5 of the specimen dispensing mechanism is not shown. The head 5 is provided with eight nozzles 5a in correspondence with the positions of the adjacent eight specimen reservoirs 15s of the electrophoretic chip 1. The specimen plate 7 has a well 7a formed therein for 384 holes (24×16) for containing test-specimens, corresponding to a spacing between the nozzles 5a of the head 5.

Though not shown, near the table 3 are arranged a voltage application part provided with electrodes at the respective positions corresponding to the reservoirs 15a, 15c, 15s, and 15w of the electrophoretic chip 1 and a detection part for detecting a specimen in the separation passage 13 of the electrophoretic chip 1.

The operations of this electrophoretic apparatus shall be described with respect to FIGS. 1 and 2A–2E as follows.

Beforehand the passages 11 and 13 are filled with a separation medium to then, arrange on the table 3, 10 sheets of the electrophoretic chips 1 each having the reservoirs 15a, 15c, 15s, and 15w filled with a buffer liquid. Although this example uses the electrophoretic chip 1 filled with a separation medium and a buffer liquid beforehand, the invention is not limited to this example; for example, near the table 3 may be provided a dispensing mechanism for injecting an electrophoretic medium or buffer liquid, so as to fill the electrophoretic chip 1 with the electrophoretic medium after the electrophoretic chips 1 are arranged on the table 3.

Using the table 3, the eight specimen reservoirs 15s into which a specimen is to be dispensed firstly are aligned with a specimen dispensing position 9.

Using the specimen dispensing mechanism, head 5 is driven to suck the test-specimens contained in the eight different wells 7a in the specimen plate 7 into the eight nozzles 5a respectively to then move the head 5 to the dispensing position 9, thus dispensing the test-specimen thus sucked in the nozzles 5a into the eight specimen reservoirs 15a simultaneously.

After the head 5 is lifted by the specimen dispensing mechanism, the table 3 is rotated to position the next eight specimen reservoirs 15s at the specimen dispensing position 9. Then, the above-mentioned specimen dispensing operations are performed to dispense the test-specimen into the eight specimen reservoirs 15s simultaneously.

The table 3 is used to sequentially align the specimen reservoirs 15s with the specimen dispensing position 9 to permit the specimen dispensing mechanism to dispense the specimens sequentially into the specimen reservoirs 15s.

Thus, the test-specimens are dispensed automatically.

After the specimens are dispensed into all the specimen reservoirs 15s of the electrophoretic chips 1 arranged on the table 3, an electrode is arranged to each of the reservoirs 15a, 15c, 15s, and 15w of each of the electrophoretic chips 1. The voltage application part is used to apply a predetermined voltage to thereby introduce the specimen contained in the specimen reservoir 15s via the specimen introducing passage 11 into the separation passage 13, through which the specimen is separated and migrates electrophoretically toward the anode reservoirs 15a in the separation passage 13.

For example, a detector for identifying for each separation passage 13, and detecting a separated component near the anode reservoir 15a of each of the separation passages 13 is arranged, thus detecting the separated component of the specimen. The detecting method, however, is not limited to this; for example, such a detector may be used that detects a distribution of separated components of a specimen within a predetermined range of the separation passage 13 after the specimen is separated and stopped in electrophoretic migration in the separation passage 13.

Thus, by the present embodiment, a plurality of electrophoretic chips with a simple passage configuration can be used to analyze a plurality of test-specimens simultaneously. By decreasing the number of the separation passages per electrophoretic chip and using a plurality of the electrophoretic chips, a high throughput can be realized. This simplifies the manufacturing of the electrophoretic chips, thus enabling increasing the yield in the production of the chips.

Although the present embodiment has used a plurality of the electrophoretic chips 1 having the same configuration, the invention is not limited to it; for example, a plurality of kinds of the electrophoretic chips 1 having different effective electrophoretic length of the separation passage may be arranged on the table 3. This enables simultaneous analysis of a plurality of test-specimens under the condition of the multiple effective electrophoretic lengths.

Although the present embodiment has arranged a plurality of the electrophoretic chips 1 on the disk-shaped table 3 constituting the electrophoretic-member holding part, the invention is not limited to it; for example, the electrophoretic-member holding part may be of any configuration as far as it can hold a plurality of electrophoretic chips at a time.

Furthermore, the electrophoretic member that can be used in the invention is not limited to such an electrophoretic chip 1 that is described in the present embodiment but may be such that is provided with only one or a plurality of separation passages.

In the present embodiment, the electrophoretic-member holding part has a function to hold a plurality of electrophoretic members on a planar member to then rotate this planar member in a plane in which these electrophoretic members are held in order to sequentially arrange each one end of the passages of the plurality of electrophoretic members sequentially at the specimen dispensing position and also is provided with a dispensing mechanism for dispensing specimens into holes corresponding to each one end of these passages arranged at that specimen dispensing position, thus enabling automatically dispensing specimens.

For detection in an electrophoretic apparatus, typically a specimen is labeled in a fluoro-metric manner beforehand and thereby detected by a fluoro-metric method.

Although there are many types of the fluorescent-light detecting device, a fluorescent-light detecting device preferred in order to realize a high S/N ratio of a detection signal is such that includes a first optical system for focusing for image formation, a light from a detecting region into a slit hole and a second optical system which is provided with at least reflection-type diffraction grating to separate a light from the slit hole in order to form an image on a detection element.

FIG. 3 is a partial perspective view for showing an embodiment of an electrophoretic apparatus equipped with such a fluorescent-light detecting device, showing only one electrophoretic chip.

The electrophoretic chip 1 is such as shown in FIG. 2, in which it is held on an electrophoretic-chip holding table 4 with its surface in which the reservoirs are formed facing upward. The electrophoretic-chip holding table 4 corresponds to the multi-chip turn table 3 of FIG. 1. The electrophoretic-chip holding table 4 is provided with a Pertier-effect temperature regulation mechanism 45 for regulating the temperature of the electrophoretic chip 1. Opposite the Pertier-effect temperature regulation mechanism 45 is provided a fan 47 for ventilateing the Pertier-effect temperature regulation mechanism 45. An electrophoretic chamber lid 49 is provided to cover the surface of the electrophoretic-chip holding table 4 on which the electrophoretic chip 1 is held.

Near the electrophoretic-chip holding table 4 are provided a polymer-injecting port 51 and a polymer-injecting syringe 53 for injecting a polymer as an electrophoretic medium into the passages and reservoirs of the electrophoretic chip 1 held on the electrophoretic-chip holding table 4.

On the surface side of the electrophoretic-chip holding table 4 on which the electrophoretic chip 1 is held is provided an electrode 55 for each of the reservoirs 15a, 15c, 15s, and 15w of the electrophoretic chip 1 for applying a voltage on the liquid contained in these reservoirs. Each electrode 55 is connected to a high-voltage supplying part 17 for supplying a voltage thereto.

As a light source of the fluorescent-light detecting device is provided an excitation light-source laser device 19. The laser device 19 may be of a variety of types such as argon (Ar) laser, kripton (Kr) laser, helium-neon (He—Ne) laser, Nd-ion solid laser made of neodium (Nd)-Yag ($Y_3Al_5O_{12}$) and the like, semiconductor laser (Laser Diode: LD), solid laser utilizing the phenomenon of optical second harmonic-wave generation (SHG).

Along an optical path for an excited light from the laser device 19 is provided a beam expander 21 for collimating the excited light. Along an optical path for the excited light from the beam expander 21 is provided a beam scanning element 23 for scanning the excited light, such as a galvanomirror or AOD (Acousto-Optics Device).

Along an optical path for the excited light from the beam scanning element 23 is provided dichroic mirror 25 for reflecting the excited light from the beam scanning element 23 toward the electrophoretic chip 1 side. The dichroic mirror 25 to be employed has such a wavelength characteristic that reflects the excited light and transmits a fluorescent light from the side of the electrophoretic chip 1.

Along an optical path for the excited light reflected by the dichroic mirror 25 is provided an objective lens 27 for converging the excited light through an opening formed in the electrophoretic chamber lid 49 to a detecting region 29 (see FIG. 2 also) of the separation passage 13 of the electrophoretic chip 1.

On the side of the dichroic mirror 25 opposite to the objective lens 27 is provided a removing filter 31 for removing excited light components. Along an optical path for the fluorescent light which passed through the removing filter 31 is provided a lens 33 for focusing for image formation, the fluorescent light to a slit 35 in which an elongated hole is formed corresponding to the detecting region 29 of the electrophoretic chip 1.

Along an optical path for the fluorescent light from an elongated hole of the slit 35 is provided a concave holographic grating (reflection type concave grating) 37 for separating the fluorescent light and focusing for image formation, it onto a receiving surface of a cooled CCD (Charge Coupled Device) 39.

To the cooled CCD 39 is connected an operating device (not shown) for processing a detection signal of the cooled CCD 39.

The fluorescent-light detecting device serves to detect separated specimens by detecting a fluorescent light at the detecting region 29 of the separation passage 13 of the electrophoretic chip 1. By separating the fluorescent light from the detecting region 29 by the grating 37, a plurality of fluorescent light wavelengths can be detected.

In this embodiment, the fluorescent-light detecting device is comprised of the excitation light-source laser device 19, the beam expander 21, the beam scanning element 23, the dichroic mirror 25, the objective lens 27, the removing filter 31, the lens 33, the slit 35, the grating 37, and the cooled CCD 39, in which the first optical system is made up of the dichroic mirror 25, the objective lens 27, the removing filter 31, the lens 33 and the slit 35 and the second optical system is made up of the grating 37.

The operations of the electrophoretic apparatus shall be described below with respect to FIGS. 3 and 2.

The electrophoretic chamber lid 49 is removed to put the electrophoretic chip 1 at a predetermined position on the electrophoretic-chip holding station 4 and then move the polymer-injecting port 51 to junction it to the reservoir 15a of the electrophoretic chip 1. The polymer contained in the syringe 53 is pushed out and injected through the polymer-injecting port 51 and the reservoir 15a into the separation passage 13 and the specimen-introducing passage 11 to the full.

A buffer is injected into the reservoirs 15a, 15c, and 15w and a specimen is injected into the specimen reservoir 15s, to all of which reservoirs is then arranged the electrode 55 to subsequently attach the electrophoretic chamber lid 49 to close the chamber. The Pertier-effect temperature regulation mechanism 45 and the fan 47 are operated to regulate the electrophoretic chip 1 and the interior of the electrophoretic chamber at a predetermined temperature.

The electrophoretic high-voltage power supply 17 is used to apply a predetermined voltage on each of the electrodes 55 to introduce the specimen contained in the specimen reservoir 15s into the specimen-introducing passage 11, after which the voltages applied on those electrodes 55 are switched to introduce the specimen at the intersection between the specimen-introducing passage 11 and the separation passage 13 into the separation passage 13. The specimen thus introduced in the separation passage 13 is permitted to electrophoretically migrate toward the anode reservoir 15a and then separated. The excitation light-source laser device 19 is operated to apply an excited light through the beam expander 21 and the beam scanning element 23 to the dichroic mirror 25. The excited light is reflected by the dichroic mirror 25 toward the objective lens 27, through which the excited light is applied into the detecting region 29. At the same time, the beam scanning element 23 scans the position at which the excited light is applied onto the dichroic mirror 25 so that the excited light may be scanned in a direction (see an arrow in FIG. 3) in which the separation passages 13 are arranged in the detecting region 29.

The light from the detecting region 29 is converged by the objective lens 27 to provide a collimated light, which is then sent to the dichroic mirror 25. The dichroic mirror 25 transmits the light from the objective lens 27 to the removing filter 31. The removing filter 31 removes the excited-light components of the light which has passed through the dichroic mirror 25 to pass only such a fluorescent light that has a predetermined wavelength to the lens 33. The lens 33 converges the fluorescent light from the removing filter 31 to an elongated hole in the slit 35. The fluorescent light, after passing through the elongated hole in the slit 35, is applied to the grating 37. The grating 37 separates the fluorescent light from the slit 35 to focus it, for image formation, onto the light receiving surface of the cooled CCD 39. Based on a detection signal from the cooled CCD 39, the specimens labeled in a fluorescent manner are detected.

The configuration of the fluorescent-light detecting device shown in FIG. 3 can be changed variously. In fact, any configuration is acceptable as far as the first optical system can focus, for image formation, a light from the detecting region into the slit hole and the second optical system is provided with at least a reflection-type diffraction grating to separate the light from the slit hole and focus it, for image formation, onto the detecting element. Also, the optical system including a light source, for applying an excited light, may be of any configuration; for example, the light source may be an LED (Light Emitting Diode).

Although the fluorescent-light detecting device shown in FIG. 3 uses as the second optical system only a concave holographic grating, which is a reflection-type concave grating, the second optical system of the invention is not limited to that but may be a combination of a concave mirror and a reflection-type planar grating.

Also, although the above detecting device employs such a system that uses a beam scanning element to scan an excited light in the detecting region as the optical system for applying an excited light to the detecting region, the optical system is not limited to that but may be any optical system as far as it can apply an excited light to the detecting region, such as an optical system for applying a line-shaped excited light to the detecting region or an optical system for applying an excited light to the detecting region from the side surface of the electrophoretic chip.

The fluorescent-light detecting device shown in FIG. 3 includes the first optical system for focusing, for image formation, a light from the detecting region to the slit hole and the second optical system provided with at least a reflection-type diffraction grating to separate the light from the slit hole and focus it, for image formation, onto an detecting element, to thereby separate the light from the detecting region using the reflection-type diffraction grating having a higher diffraction efficiency than the that of a transparent diffraction grating thus enabling realizing a high S/N ratio for the detection signal at the detecting element Furthermore, even in detection of a fluorescent light in such a detecting region that covers a plurality of detecting positions, the cross-talk can be reduced by the high image-formation characteristics of the reflection-type diffraction grating.

By providing such a configuration that a reflection type concave grating is provided as the reflection-type diffraction grating and also that the second optical system is comprised of only a reflection-type concave grating, it is possible to separate a light from the slit hole and focus it, for image formation, onto the detecting element without using such optical systems as the concave mirror. This simplifies the configuration of the device.

Figure 4:
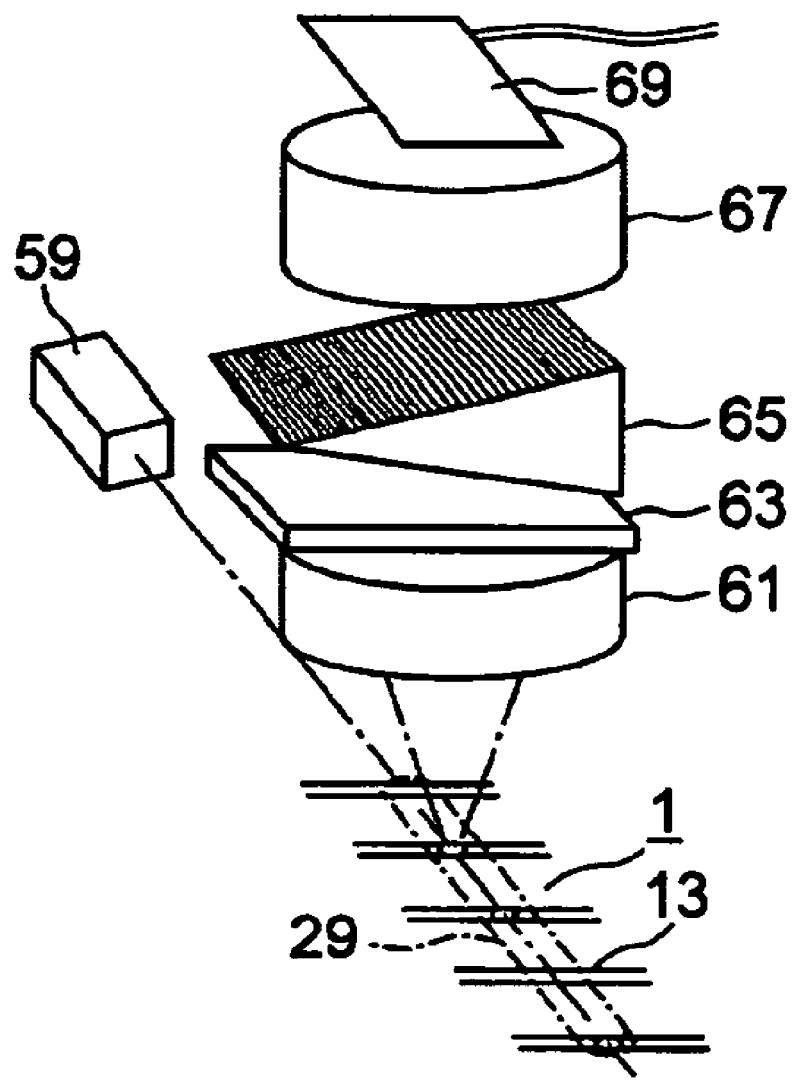
FIG. 4 is a perspective view for showing another fluorescent-light detecting device.

FIG. 4 is a perspective view for showing another fluorescent-light detecting device.

In the electrophoretic chip 1 is formed a plurality of the separation passages 13, at a predetermined position along which is provided the linear detecting region 29. A laser device 59 provided beside the electrophoretic chip 1 causes an excited light to be applied to the detecting region 29 and simultaneously to a plurality of the separation passages 13.

A convergence lens 61 provided above the electrophoretic chip 1 collimates the light from a specific one of the separation passages 13 in the detecting region 29. This collimated light is sent through a removing filter 63 for removing a laser beam to a transparent diffraction grating 65. The transparent diffraction grating 65 separates the collimated light from the removing filter 63 to focus it, for image formation, onto a CCD 69 through an image-forming lens 67. The lights with different wavelength are focused, for image formation, at different positions on the CCD 69. Based on a detection signal from the CCD 69 is calculated an intensity of a predetermined fluorescent-light wavelength. By thus checking the intensity of the fluorescent-light wavelength, it is possible to decide the presence of a fluorescent material which emits a fluorescent light in the detecting region 29.

In the fluorescent-light detecting device shown in FIG. 4, by moving toward the detecting region 29 the electrophoretic chip 1 or the optical system including the convergence lens 61, the removing filter 63, the transparent diffraction grating 65, the image forming lens 67 and the CCD 69, the fluorescent light is detected over a plurality of the separation passages 13 in the detecting region 29.

In the electrophoretic apparatus using an electrophoretic chip, when a voltage is applied to guide a specimen injected in the specimen reservoir to an intersection between the specimen-introducing passage and the separation passage, the specimen should be distributed uniformly throughout along the specimen-introducing passage; that is, such injection conditions for guiding a sufficient amount of the specimen to the intersection between the specimen-introducing passage and the separation passage as a value of a voltage applied across the passages and a voltage application time or a temperature must be discussed for each passage design or specimen. Conventionally, the injection conditions have been discussed using a monitor different from the electrophoretic apparatus.

However, when the electrophoretic chip is mounted to the electrophoretic apparatus and a voltage is applied to guide a specimen to an intersection between the specimen-introducing passage and the separation passage of the electrophoretic chip under the injection condition obtained using the above-mentioned monitor, the sample sometimes cannot be distributed uniformly throughout the specimen-introducing passage by some disorder. Although the result of measurement obtained when the specimen is injected into the separation passage under the condition that the specimen is not distributed uniformly throughout the specimen-introducing passage is deficient in reliability, the specimen distribution along the specimen-introducing passage when it is injected therein could not be confirmed.

The following will describe an embodiment of an electrophoretic apparatus provided with such a specimen-injection monitor mechanism that detects a specimen distribution along the specimen-injection passage including at least the intersection between the specimen-inject passage and the separation passage to improve the reliability of the measurement result.

Figure 5:
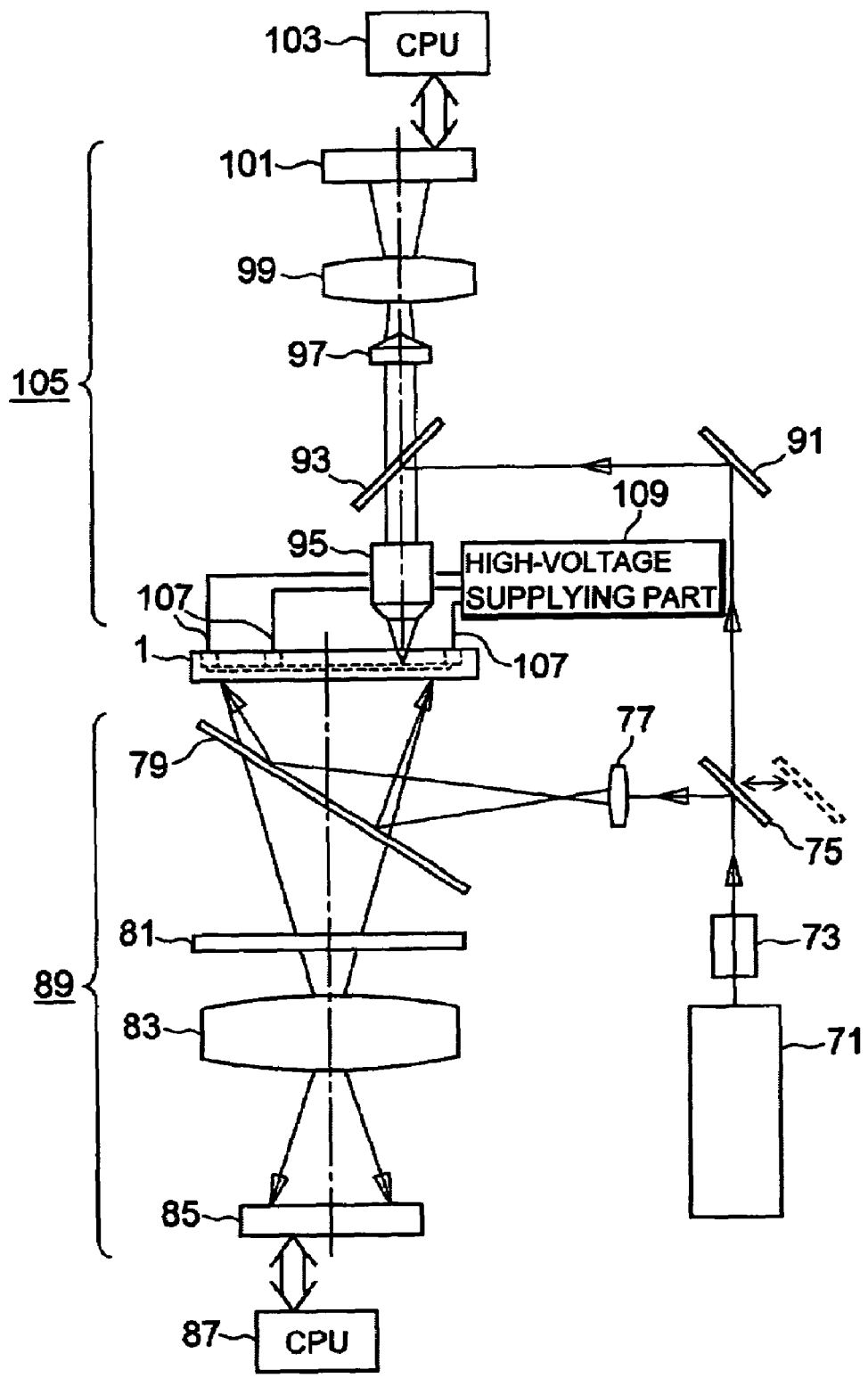
FIG. 5 is a schematic configuration diagram for showing an embodiment provided with a specimen-injection monitor mechanism.

FIG. 5 is a schematic configuration diagram for showing one embodiment of an electrophoretic apparatus provided with such a specimen-injection monitor mechanism. The electrophoretic chip 1 shown in FIG. 5 is the same as that of FIG. 2.

The electrophoretic chip 1 is held on a chip holding station (not shown) with its surface in which the reservoirs are formed facing upward. The chip holding station is provided with a temperature regulating mechanism for regulating the temperature of the chip 1.

Such an excitation light-source laser device 71 is provided that is commonly used in a separation-peak detecting optical system and a specimen-injection monitor optical system which shall be described later. The laser device 71 may be of a variety of types such as argon (Ar) laser, kripton (Kr) laser, helium-neon (He—Ne) laser, Nd-ion solid laser made of neodium (Nd)-Yag ($Y_3Al_5O_{12}$) and the like, semiconductor laser (Laser Diode: LD), solid laser utilizing the phenomenon of optical second harmonic-wave generation (SHG).

Along an optical path for an excited light from the laser device 71 is provided a beam expander 73 for collimating the excited light. Along an optical path for the excited light from the beam expander 73 is provided a movable reflection mirror 75 which is moved between a position indicated by a solid line along the optical path and a position indicated by a broken line out of the optical path.

Along an optical path for the excited light reflected by the movable reflection mirror 75 is provided a lens 77 for expanding the excited light. Along an optical path for the excited light from the lens 77 is provided a dichroic mirror 79 arranged on the side of the bottom of the chip 1 (opposite the surface in which the reservoirs are formed) for reflecting the excited light from the lens 77 toward the bottom of the chip 1. The dichroic mirror 79 to be employed has such a wavelength characteristic that reflects an excited light but transmits a fluorescent light from the side of the chip 1.

On the side of the dichroic mirror 79 opposite to the chip 1 is provided a spectroscopic filter 81. The spectroscopic filter 81 transmits only such a light component that has a predetermined wavelength of the fluorescent light from the chip 1 which has passed through the dichroic mirror 79. The specifications of the dichroic mirror 79 and the spectroscopic filter 81 are determined by a fluorescent material used for labeling the specimen and a wavelength of the excited light oscillated by the laser device 71.

Along an optical path for the fluorescent light which has passed through the spectroscopic filter 81 is provided a lens 83 for focusing for image formation, the fluorescent light on a light receiving surface of the CCD 85.

To the CCD 85 is connected a CPU (Central Processing Unit) 87 for controlling operations thereof and processing a detection signal of the CCD 85.

The movable reflection mirror 75, the dichroic mirror 79, the spectroscopic filter 81, the lens 83, and the CCD 85 make up a specimen-injection monitor optical system 89. The monitor optical system 89 detects a fluorescent label along the specimen-introducing passage 11 and the separation passage 13 of the chip 1 to thereby detect a specimen distribution at these passages 11 and 13.

In the monitor optical system 89, the lens 77 may be omitted in case that the diameter of the output light of the beam expander 73 and the design of the passages of the chip 1 as far as an excited light can be at least applied to the intersection between these specimen-introducing passage 11 and separation passage 13.

The laser device 71, the beam expander 73, the CPU 87, and the monitor optical system 89 make up the specimen-injection monitor mechanism.

A reflection mirror 91 is provided along an optical path for an excited light from the beam expander 73 when the movable reflection mirror 75 is at a position indicated by the broken line. Along an optical path for the excited light reflected by the reflection mirror 91 is provided a dichroic mirror 93 which is arranged on the surface side of the chip 1 (in which the reservoirs are formed) for reflecting the excited light from the reflection mirror 91 toward that surface of the chip 1. The dichroic mirror 93 to be employed has such a wavelength characteristic that reflects an excited light and transmits a fluorescent light from the side of the chip 1.

Along an optical path for the excited light reflected by the dichroic mirror 93 is provided an objective lens 95 for converging the excited light in a detected position along the separation passage 13 of the chip 1.

On the side of the dichroic mirror 93 opposite to the objective lens 95 is provided a spectroscopic element 97. The spectroscopic element 97 separates a fluorescent light from the chip 1 which has passed through the objective lens 95 and the dichroic mirror 93. The spectroscopic element 97 employed may be, for example, a combination of a spectroscopic filter panel and a wedge prism or a transmission type grating.

Along an optical path for the fluorescent light which has passed through the spectroscopic element 97 is provided a lens 99 for focusing for image formation, that fluorescent light on a light receiving surface of a CCD 101.

To the CCD 101 is connected a CPU 103 for controlling operations thereof and processing a detection signal thereof.

The reflection mirror 91, the dichroic mirror 93, the objective lens 95, the spectroscopic element 97, the lens 99, and the CCD 101 make up a separation-peak detecting optical system 105. The detecting optical system 105 detects specimens separated when a fluorescent label is detected at a detected position along the separation passage 13 of the chip 1. By separating a light from the detected position using the spectroscopic element 97, a plurality of kinds of fluorescent wavelength can be detected.

The laser device 71, the beam expander 73, the CPU 103, and the detecting optical system 105 make up the detecting mechanism.

On the surface side of the chip 1 is provided an electrode 107 for each of the reservoirs 15a, 15c, 15s, and 15w of the chip 1 for applying a voltage on a liquid contained in these reservoirs. Each electrode 107 is connected to a high-voltage supplying part 109 for supplying a high voltage to the electrode 107. The high-voltage supplying part 109 is connected to the CPU 87, which controls its operations.

The electrode 107 and the high-voltage supplying part 109 make up a voltage-supplying mechanism, while the CPU 87 implements a control part.

Figure 6:
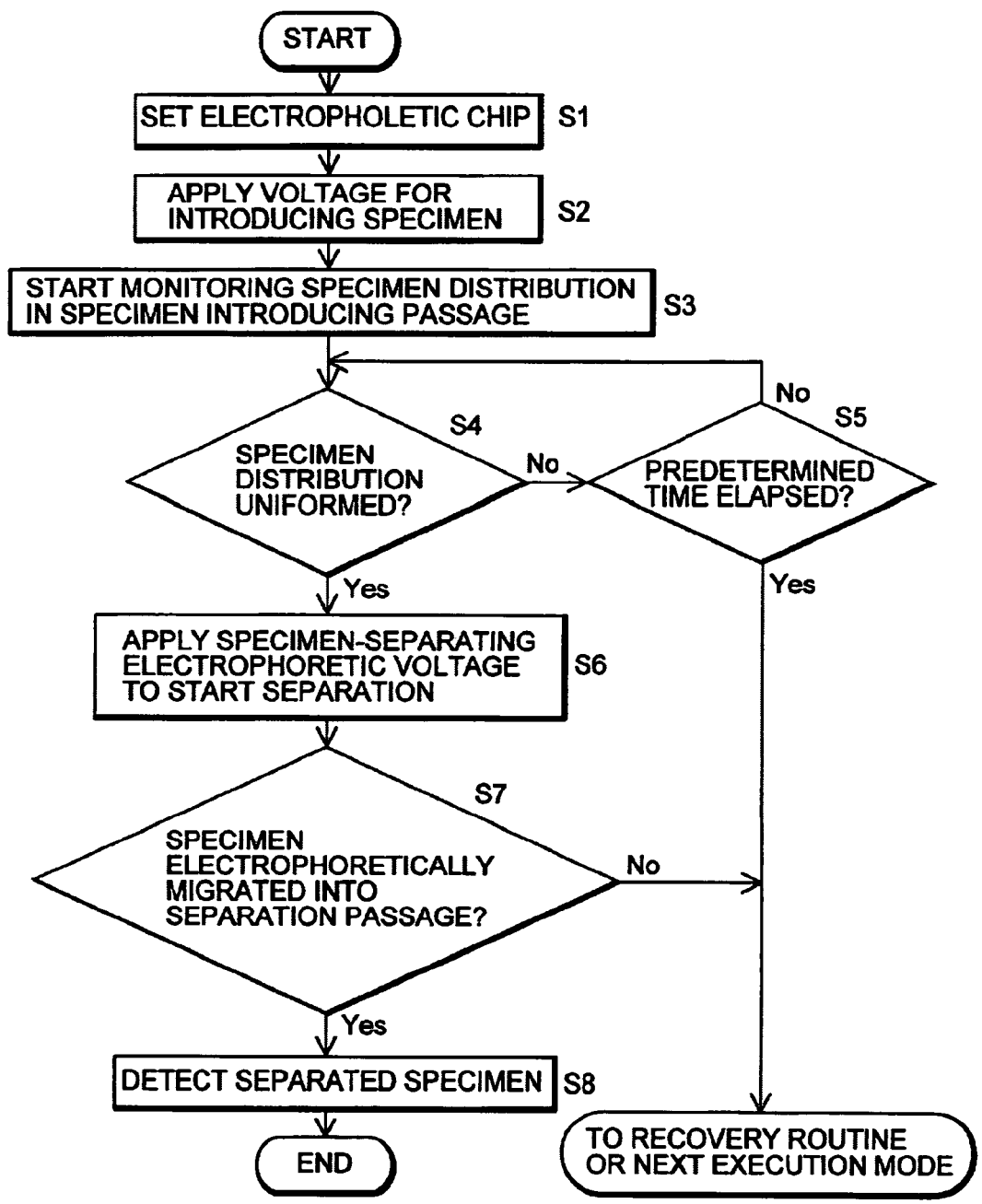
FIG. 6 is a flowchart for showing operations of the embodiment of FIG. 5.

FIG. 6 is a flowchart for showing the operations of this embodiment FIG. 7 is a conceptual plan view for showing one passage of the chip 1 as well as a conceptual expanded diagram for showing an intersection between a specimen-injection passage and a separation passage when a specimen is introduced. The operations of this embodiment shall be described below with reference to FIGS. 5–7.

An electrophoretic medium is injected into the specimen-injection passage 11 and the separation passage 13, a buffer liquid is injected into the reservoirs 15a, 15c, and 15w, and a specimen is injected into the reservoir 15s to then mount the chip 1 thus filled with these on the chip-holding station (step S1).

An electrode 107 is put forward into the reservoirs 15a, 15c, 15s, and 15w to cause a high-voltage supplying part 109 to apply through the electrode 107 a specimen introducing voltage on these reservoirs 15a, 15c, 15s, and 15w under the pre-discussed injection condition (step S2). Then, the specimen thus injected in the reservoir 15s starts to spread in the specimen-introducing passage 11.

The monitor optical system 89 is used to monitor a specimen distribution in the specimen-introducing passage 11 (step S3).

The operations shall be described as follows: Firstly, the movable reflection mirror 75 is moved to the solid line position to cause the laser device 71 to oscillate an excited light. The excited light from the laser device 71 is collimated by the beam expander 73. The excited light thus collimated is reflected by the movable reflection mirror 75 and made incident to the monitor optical system 89. The excited light from the movable reflection mirror 75 is expanded by the lens 77 and then reflected by the dichroic mirror 79 to be applied to the back side surface of the chip 1. Thus, the excited light is applied all over to the specimen-introducing passage 11 and to the separation passage 13.

The spectroscopic filter 81 transmits toward the lens 83 only a fluorescent-light component with a predetermined wavelength of a fluorescent light from the chip 1 applied to the spectroscopic filter 81 through the dichroic mirror 79 so that thus transmitted fluorescent light may be focused by the lens 83 onto the CCD 85 for image formation. The CPU 87 converts a detection signal of the CCD 85 into an image file a data to thereby monitor the specimen distribution.

The CPU 87 decides whether the specimen distribution is uniformed in the specimen-introducing passage 11 (step S4). Thus, it can be decided whether such an amount of the specimen is introduced to the intersection 10 that is enough for separation and detection.

If it is decided that the specimen distribution is not uniformed at step S4 (NO), the CPU decides whether a predetermined time has elapsed after the specimen introducing voltage was applied (step S5). If the predetermined time has not elapsed yet (NO), the process returns to step S4. Otherwise (YES), the CPU 87 control the high-voltage supplying part 109 so as to stop voltage application, thus making a shift to a recovery routine or the next execution mode.

If it is decided that as shown in the expanded diagram of the intersection 10 in FIG. 7 the specimen distribution is uniformed in the specimen-introducing passage 11 and also is decided as uniformed at step S4 (YES), the high-voltage supplying part 109 switches the voltages applied on the reservoirs 15a, 15c, 15s, and 15w to apply an electrophoretic voltage for specimen separation, thus starting electrophoretic migration of the specimen (step S6).

In this case, the CPU 87 is continuously engaged in the monitoring of the specimen distribution in the specimen-introducing passage 11 using the monitor optical system 89, to decide whether the specimen present at the intersection 10 is injected into the separation passage 13 (step S7).

If it is decided that the specimen is not yet injected into the separation passage 13 at step S7 (NO), the CPU 87 controls the high-voltage supplying part 109 to stop voltage application, thus making a shift to the recovery routine or the next execution mode.

When it is decided that the specimen is already injected into the separation passage 13 at step S7 (YES), application of the electrophoretic voltage is continued to separate the specimen for electrophoretic migration.

The detecting optical system 105 is used to detect the specimen that has arrived at the detection position (step S8).

The operations shall be described as follows: after it is confirmed that the specimen is already injected into the separation passage 13 at step S7, the movable mirror 75 is moved to the broken-line position to apply an excited light from the beam expander 73 onto the reflecting mirror 91. The excited light from the beam expander 73 is reflected by the reflecting mirror 91 and made incident into the detecting optical system 105. The excited light from the movable reflection mirror 75 is reflected by the dichroic mirror 93 toward the surface side of the chip 1 and then converged by the objective lens 95 to be applied from the surface side of the chip 1 to the detection position of the separation passage 13.

The fluorescent light from the detection position of the separation passage 13 is applied through the objective lens 95 and the dichroic mirror 93 onto the spectroscopic element 97. The spectroscopic element 97 separates the fluorescent light from the detection position of the separation passage 13, which is then focused, for image formation, onto the CCD 101 through the lens 99. The CPU 103 converts a detection signal of the CCD 101 into an image file as data for waveform processing, thus detecting the separated specimen.

After specimen separation, the high-voltage supplying part 109 stops supplying the voltage.

Thus, by using the monitor optical system 89 provided to the apparatus, to monitor a specimen distribution in the specimen-introducing passage 11, especially around the intersection 10 between the specimen-introducing passage 11 and the separation passage 13, it is possible to decide at step S4 of FIG. 6 whether a sufficient amount of the specimen is introduced to the intersection 10 when a voltage is applied on the reservoirs to move the specimen there, so that if it is decided that a sufficient amount of the specimen is not introduced at the intersection 10 yet, the measurement can be stopped to thereby improve the reliability of the measurement results. Further, at step S8 in FIG. 6, it can be decided whether the specimen present at the intersection 10 is introduced into the separation passage 13 in electrophoretically migration, so that if it is not migrating electrophoretically, the measurement can be stopped to improve the reliability of the measurement results.

As in the embodiment shown in FIG. 5, by providing the specimen-introduction monitor mechanism and the detecting mechanism with fluorescent-light detecting optical systems and also providing these fluorescent-light detecting optical systems with an excitation light source common to them, the apparatus can be minimized and reduced in costs as well as running costs as compared to a case where it is provided each of them. The possible aspect, however, is not limited to the above, an excitation light source may be provided for each of the monitor optical system 89 and the detecting optical system 105. In this case, the movable reflection mirror 75 and the reflecting mirror 91 become unnecessary.

Also, although in the embodiment of FIG. 5 the monitor optical system 89 constituting the sample-injection monitor mechanism covers all over the specimen-introduction passage 11 and the separation passage 13 for detection, the invention is not limited to it; for example, the specimen-introduction monitor mechanism may only need to cover, for detection, part of the whole of the specimen-introduction passage including the intersection between the specimen-introduction passage and the separation passage.

The electrophoretic chip 1 is applicable regardless of being formed therein by one separation passage 13 or many separation passages.

Figure 8A:
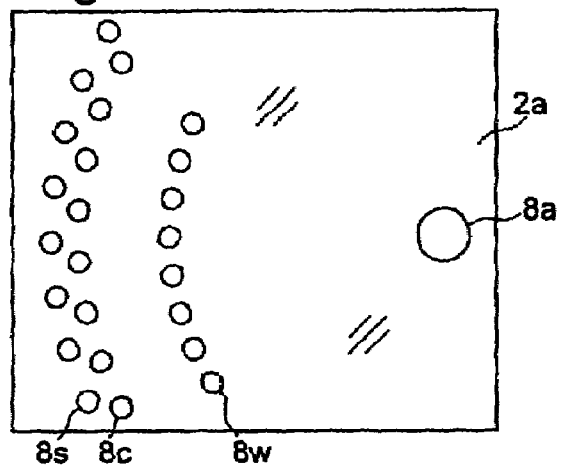
Figure 8B:
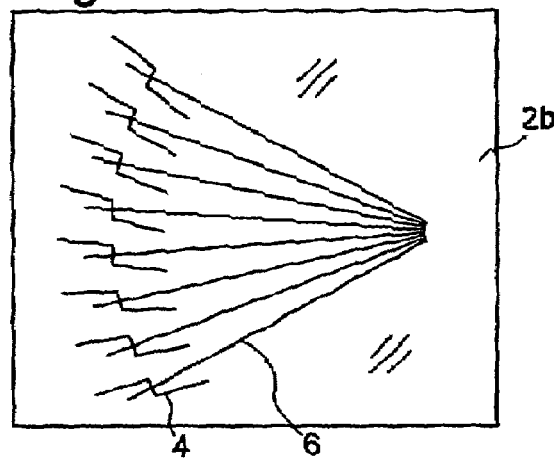

FIG. 8, similar to FIG. 2, shows top views for showing an electrophoretic chip in which many separation passages are formed.

The electrophoretic chip 2 is comprised of one pair of substrates 2a and 2b made of a transparent inorganic material (e.g., glass, quartz, silicon) or plastic.

On the surface of one substrate 2b are formed eight pairs of specimen-introduction passages 4 and separation passages 6 mutually intersecting using a semiconductor photo-lithographic technology or a micro-machining technology. Each pair of the passages 4 and 6 are arranged in a sector shape with, using a pivot, one end side of the separation passage 6 opposite to the side intersecting with the specimen-introduction passage 4, thus avoiding intersecting with the passages of other pairs. The specimen-introduction passage 4 is formed hook-shaped to reduce the area of the chip 2.

The other substrate 2a has through holes serving as an anode reservoir 8a, a cathode reservoir 8c, a specimen reservoir 8s, and a waste reservoir 8w at the positions corresponding to the ends of the passages 4 and 6. The reservoirs 8c, 8s, and 8w are provided for each pair of the passages 4 and 6. The anode reservoir 8a is common on the side of one end of the separation passage 6 of each pair on the side of the pivot in the sector-shape arrangement.

The chip 2 is used in a state where both of its substrates 2a and 2b are connected on one another. In the chip 2, a position where a separated specimen is detected is near one end of the separation passage 6 of each pair on the side of the pivot in a sector-shaped arrangement.

When measurement is conducted by mounting the chip 2 on such an electrophoretic apparatus as shown in FIG. 5, the electrode 107 of the apparatus needs to be provided corresponding to the arrangement of the reservoirs 8a, 8c, 8s, and 8w. Furthermore, as for the detecting optical system 105, for example, along an optical path between the reflecting mirror 91 and the dichroic mirror 93 must be provided with such a beam scanning element as a galvano-mirror or AOD to thereby scan an excited light at a linear detection position, and the spectroscopic element 97, the lens 99 and the CCD 101 must be changed to those enabling detecting while discriminating between the eight separation passages 6.

By using, in electrophoresis, the electrophoretic apparatus shown in FIG. 5 thus modified corresponding to chip 2, it is possible to use the monitor optical system 89 to monitor a specimen distribution in the specimen-introduction passage 4 and the electrophoretic migration of the specimen toward the separation passage 6.

FIG. 9 is a graph illustration for showing a detection signal obtained when the specimen is labeled with four kinds of fluorescent materials with different wavelengths and separated and detected by the chip 2. The horizontal axis (x-axis) indicates the No. (channel No.) of the separation passage 6 and the vertical axis (y-axis), four kinds of spectra. In FIG. 9, the detection signals of the four separation passages 6 are indicated.

In FIG. 9, a circle gives an intensity of a separated fluorescent light at a detected position thereof. The black circle, the dotted circle and the white circle indicate the intensities of the detection signals in order of intensity in each channel.

Different specimens are injected into the specimen reservoirs 8s of the chip 2 and a voltage is applied to these reservoirs to thereby guide these specimens to the intersection between the specimen-introduction passage 4 and the separation passage 6 of each pair and then apply electrophoretic voltages on these reservoirs, thus injecting the specimens present at the intersection into the separation passage 6. In each of the separation passages 6, the specimen is separated and electrophoretically migrates toward the anode reservoir 8a. The specimen components that were separated and arrived at the detection position are identified using the four kinds of fluorescent materials.

Figure 10:
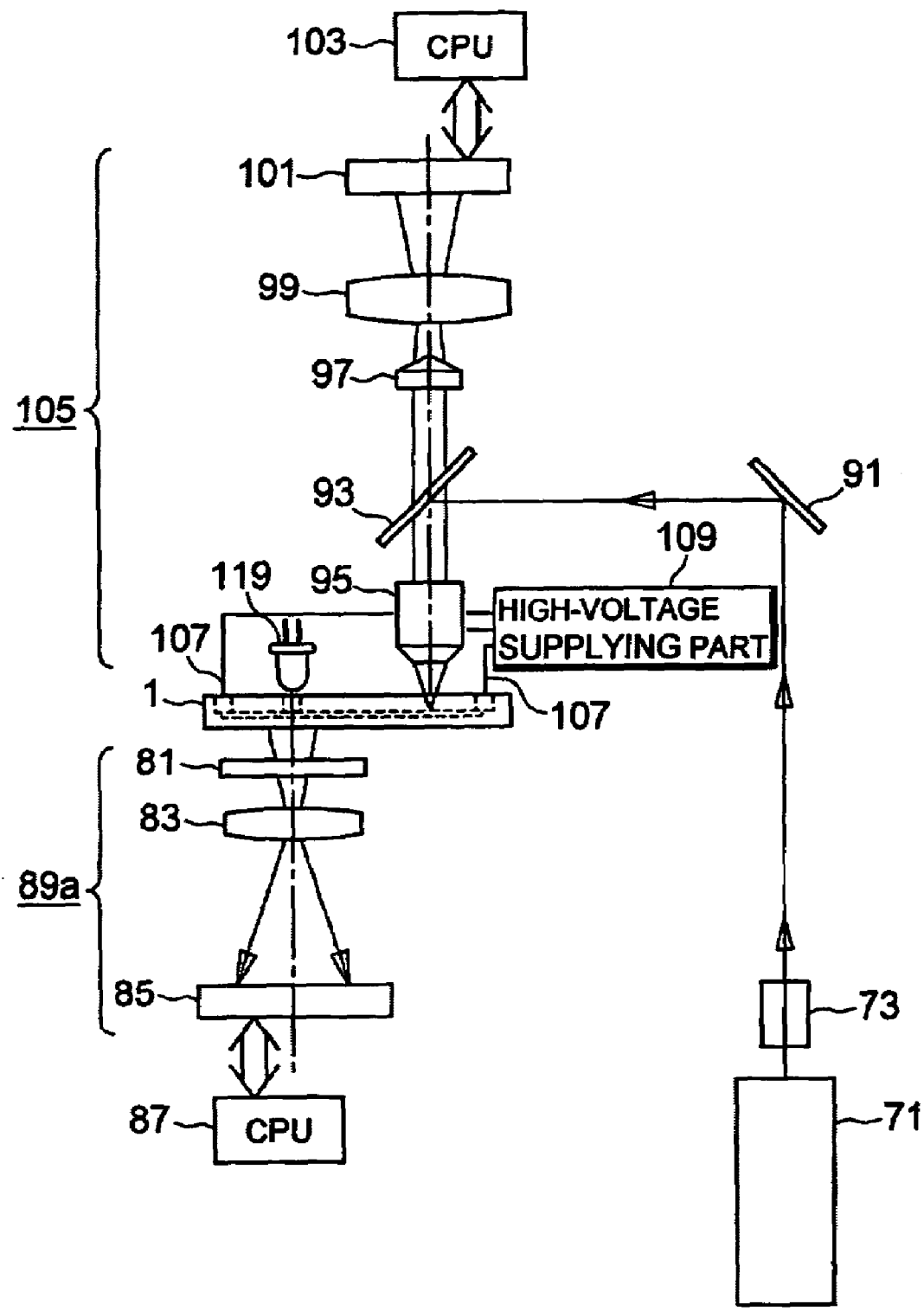
FIG. 10 is a schematic configuration diagram for showing an embodiment provided with another specimen-injection monitor mechanism.

FIG. 10 is a schematic configuration diagram for showing another embodiment of the electrophoretic apparatus of the invention. The electrophoretic chip 1 shown in FIG. 10 is the same as that shown in FIG. 2. The same elements as those of FIG. 5 are indicated by the same reference numerals and so omitted in description.

On the chip 1 is held the chip holding station (not shown). The excitation light-source laser device 71, the beam expander 73, the CPU 103, the separation-peak detecting optical system 105 (including the reflecting mirror 91, the dichroic mirror 93, the objective lens 95, the spectroscopic element 97, the lens 99 and the CCD 101), the electrode 107 and the high-voltage supplying part 109 are the same as those of the embodiment of FIG. 5. The electrodes 107 corresponding to the specimen reservoir and the waste reservoir are omitted in the figure. Also, the reflecting mirror 91 may be omitted to inject an excited light from the beam expander 73 directly to the dichroic mirror 93.

An LED 119 is disposed as the excitation light-source at a position corresponding to an intersection between the specimen-introduction passage 11 and the separation passage 13 on the surface side of the chip 1. As the LED 119 a blue LED, for example, may be used with an oscillation frequency of 480 nm. The LED used in the invention, however, is not limited to a blue one and such an LED that emits other colors, that is, lights of other wavelengths may be used.

The spectroscopic filter 81 is disposed at a position corresponding to the intersection between the specimen-introduction passage 11 and the separation passage 13 on the back side surface of the chip 1. The spectroscopic filter 81 transmits only such a light component that has a predetermined fluorescent wavelength of a fluorescent light from around the intersection 10 of the chip 1. The specifications of the spectroscopic filter 81 are determined by the fluorescent material used in labeling of the specimen and the wavelength of an excited light emitted by the LED 119.

Along an optical path for the fluorescent light, which passed through the spectroscopic filter 81, is provided the lens 83 for focusing, for image formation, the fluorescent light on a light receiving surface of the CCD 85.

To the CCD 85 is connected the CPU 87 for controlling the operations of the CCD 85 and processing its detection signal.

The LED 119, the spectroscopic filter 81, the lens 83 and the CCD 85 constitute a specimen-injection monitor optical system 89a. The monitor optical system 89a detects a fluorescent label around the intersection between the specimen-introduction passage 11 and the separation passage 13 of the chip 1 to thereby detect a specimen distribution in the passages 11 and 13 near the intersection.

The LED 119, the monitor optical system 89a, and the CPU 87 constitute the specimen-injection monitor mechanism.

Figure 8C:
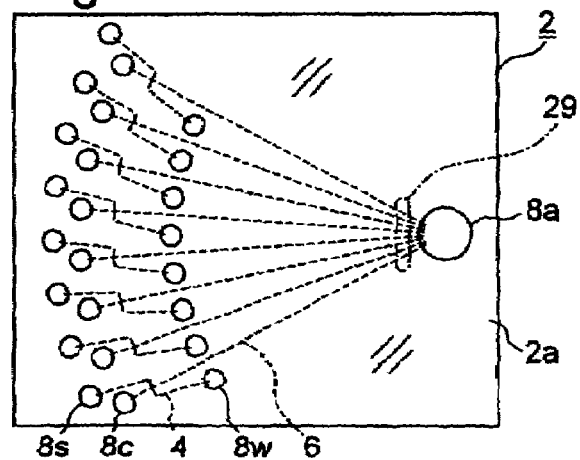

In this embodiment, when a voltage is being applied on the reservoirs to guide a specimen injected in the specimen reservoir to the intersection, the LED 119 is turned ON to then use the monitor optical system 89a in order to monitor a specimen distribution in the specimen-introduction passage 11, especially, around the intersection between the specimen-introduction passage 11 and the separation passage 13. This enables, like in the embodiment of FIG. 5, deciding whether a sufficient amount of the specimen is already introduced to the intersection, thus improving the reliability of the measurement result The embodiment of FIG. 10 can be applied also to a single-channel electrophoretic chip and a multi-channel electrophoretic chip. For example, when the chip 2 shown in FIG. 8C is used, by arranging eight LEDs side by side corresponding to positions of the intersections between the specimen-introduction passagea 4 and the separation passage 6, it is possible to apply an excited light to each of the intersections, thus monitoring a specimen distribution at the intersections.

Although in the embodiment of FIG. 10 the LED 119 is disposed corresponding to the position of the intersection between the specimen-introduction passage 11 and the separation passage 13 of the chip 1 to apply an excited light from the LED 119 directly to the intersection 10, a convergence lens may be disposed between the LED 119 and the chip 1, for example, to apply the excited light from the LED 119 therethrough to the intersection or, in the configuration shown in FIG. 5, the movable reflection mirror 75 may be omitted and, instead, an LED may be disposed on the side of the lens 77 opposite to the dichroic mirror 79 to thereby apply an excited light from the LED through the lens 77 and the dichroic mirror 79, thus applying the excited light from the LED through the optical system to the chip 1.

Such an embodiment of FIG. 10 that is provided with the detecting optical system using an LED as its light source can reduce the cost of the light source itself and hence the costs of the specimen-injection monitor mechanism. Furthermore, by arranging an LED array corresponding to a layout at a site where the specimen is injected, there is no need for a complicated optical system for illumination, thus enabling further reducing the costs of the specimen-injection monitor mechanism.

The electrophoretic chip that can be used in an electrophoretic apparatus according to the embodiment of FIGS. 5 and 10 is not limited to such that has one passage formed as intersecting with the separation passage. For example, it may be such an electrophoretic chip that has formed therein a separation passage with no intersection with any other passages, that has a plurality of passages intersecting with each other as the separation passage, that has a large size, or that has any other various designs of the passage. Corresponding to the design of the passages of the electrophoretic chip, however, it is necessary to modify the voltage supplying mechanism, the detecting mechanism, and the specimen-injection monitor mechanism.

Although in the embodiment shown in FIGS. 5 and 10 the specimen-injection monitor mechanism and the detecting mechanism use a fluorescent-light detecting optical system, the invention is not limited to it, and in place of the specimen-injection monitor mechanism and the detecting mechanism, any other mechanism using an absorptio-metric or electric-conductivity method or the like may be utilized.

By providing an electrophoretic chip used with mutually intersecting specimen-injection passage and separation passage as its passages and using a voltage supplying mechanism to apply a voltage for guiding a specimen to an intersection between the specimen-injection and separation passages so that if, subsequently, the specimen distribution is not uniformed yet even after a predetermined time has elapsed within a predetermined range along the specimen-injection passage detected by the specimen-injection monitor mechanism, a control part, further provided, may once stop the apparatus, and it can be decided automatically whether the electrophoretic migration of the specimen is acceptable, thus controlling that migration.

Although in the embodiments shown in FIGS. 5 and 10 the CPU 87 and the CPU 103 are provided for the monitor optical systems 89 and 89a and the detecting optical system 105 respectively, one CPU may be used to perform the functions of both the CPU 87 and CPU 103.

By the embodiments shown in FIGS. 5 and 10, it is also possible to discuss the conditions for injecting the specimen. By changing the temperature of the chip 1, the voltages fed to the reservoirs by the high-voltage supplying part 109, and the time lapse for the voltage application on these reservoirs, a specimen distribution in the specimen-introduction passage 11 can be monitored using the monitor optical system 89 or 89a under various conditions. This enables discussing optimal injection conditions.

Conventionally, manual operations have been used to fill the micro-chip with an electrophoretic medium, to remove the electrophoretic medium from the reservoir, to inject a specimen and a buffer liquid into the reservoirs, to remove the specimen from the reservoirs after injected in the separation passage, and to inject the buffer liquid into the reservoirs after the specimen removal. These operations, however, are very troublesome for the operator who must do them by hand using a syringe and the like.

Figure 11:
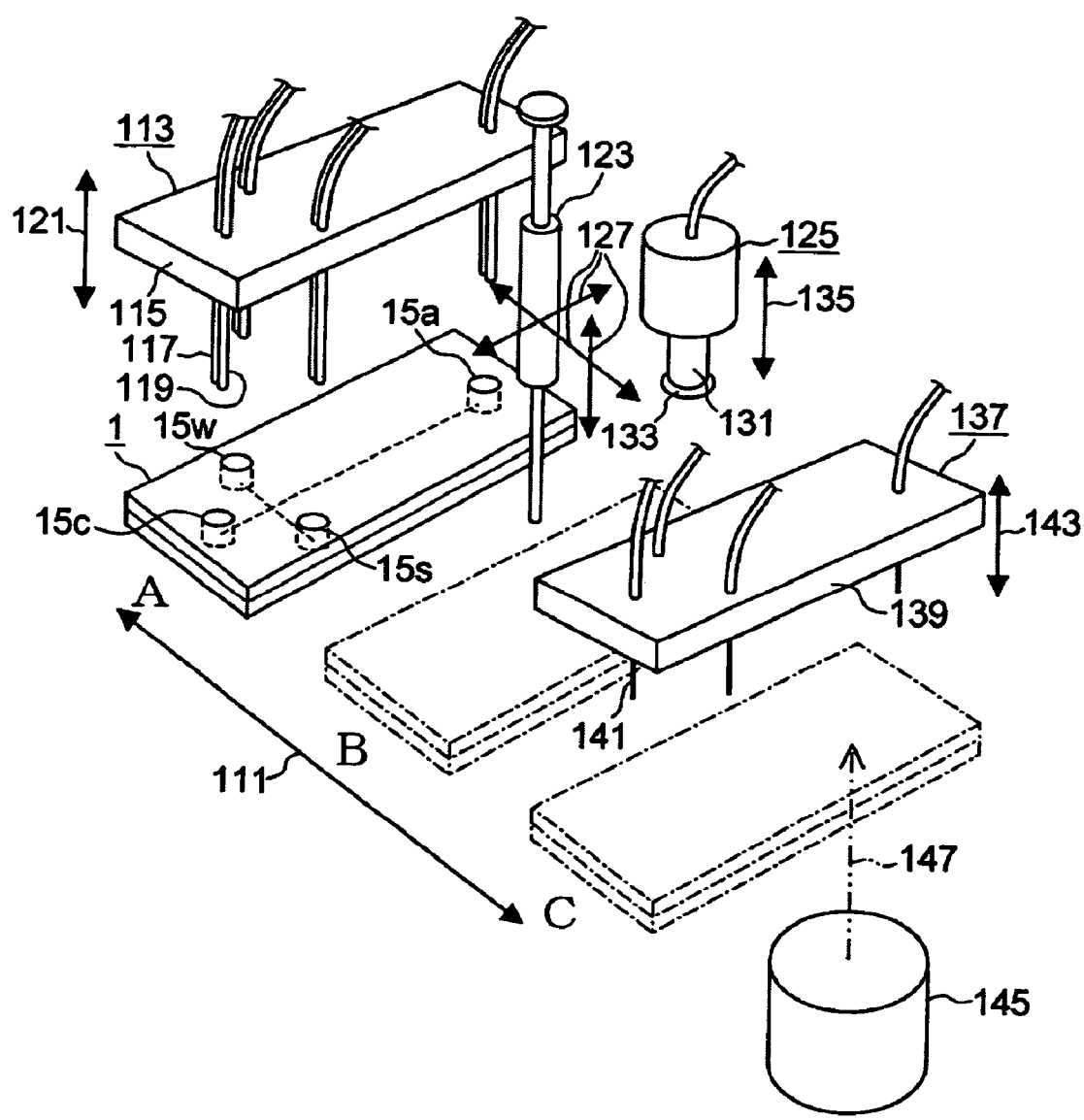
FIG. 11 is a perspective view for showing a schematic configuration of an embodiment in which operations are automated.
Figure 14A:
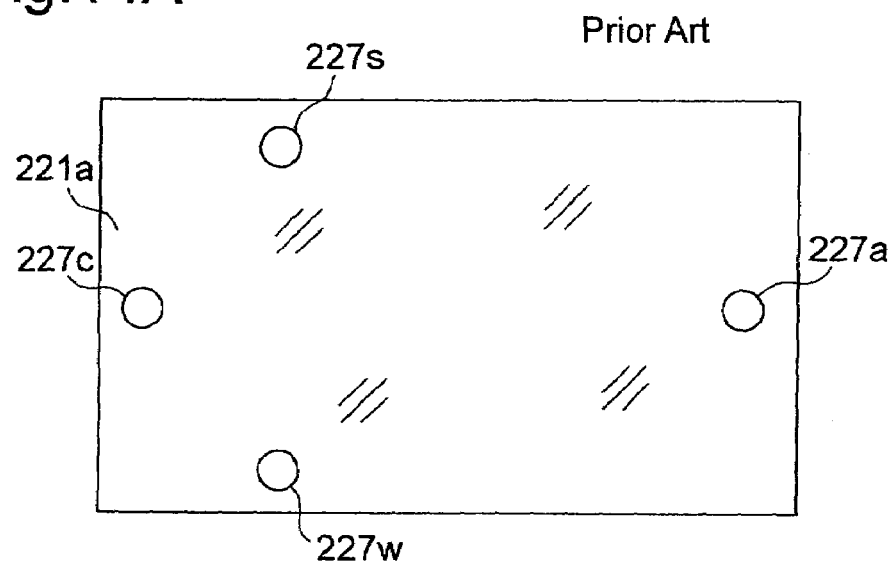
FIGS. 14A–14C are illustrations for showing a prior art electrophoretic chip, FIG. 14A of which is a top view for showing one substrate.
Figure 14B:
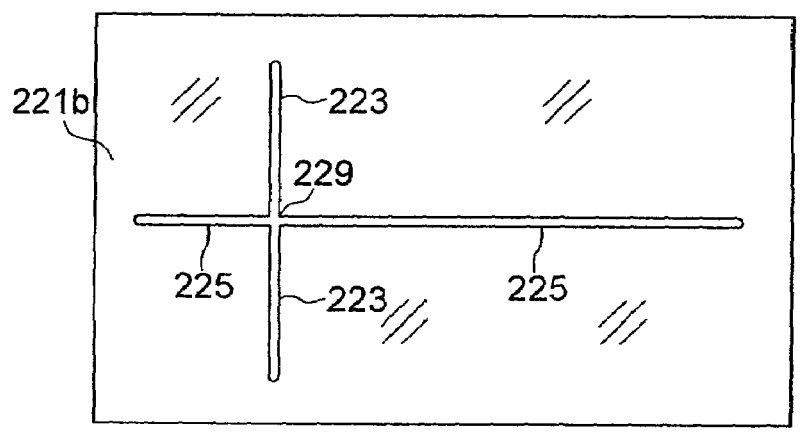
Figure 14C:
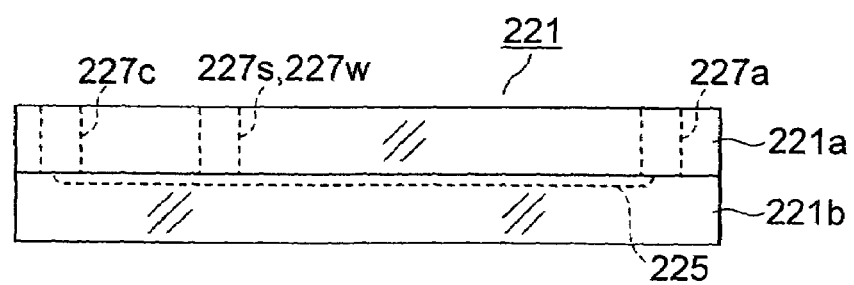

An embodiment of the electrophoretic apparatus to solve this problem by automating those operations shall be shown in FIG. 11. FIG. 11 is a perspective view for showing a schematic configuration of the embodiment. The electrophoretic chip 1 is the same as that shown in FIG. 2, in which it is indicated, however, as having one separation passage and one specimen-introduction passage which intersect with each other in order to make the description simple.

A chip-holding mechanism (not shown) is provided to hold the electrophoretic chip 1, so that the chip 1 held thereon is moved by a moving mechanism provided to the chip-holding mechanism in an arrow direction 111 between positions A, B, and C in the figure.

Above the position A is provided a port 113 for sucking an electrophoretic medium and injecting a buffer liquid. The port 113 includes a nozzle-fixing member 115 and four pairs of a suction nozzle 117 and a discharge nozzle 119 which are fixed to the member 115 corresponding to an arrangement of the reservoirs 15$a$, 15$c$, 15$s$, and 15$w$ when the chip 1 is positioned at the position A. The suction nozzle 117 and the discharge nozzle 119 are connected to independent syringes (not shown) respectively. Furthermore, the port 113 is provided with an elevation mechanism (not shown) for lifting/lowering the member 115 in an arrow direction 121 in the figure. The elevation mechanism lowers the member 115 so that the tips of the nozzles 117 and 119 may advance into the reservoirs 15$a$, 15$c$, 15$s$, and 15$w$ when the chip 1 is at the position A.

The electrophoretic medium-suction-and-buffer liquid-injection port 113, the syringes, and the elevation mechanism constitute an electrophoretic medium-suction mechanism and a buffer liquid-injection mechanism.

As the nozzles 117 and 119 a resin-made capillary, for example, may be used. The nozzles 117 and 119, however, are not limited to a resin-made capillary; for example, such a capillary may be used that is made of any other materials such as glass capillary.

Above the position B are provided a specimen loading syringe 123 constituting the specimen-injection mechanism and an electrophoretic-medium loading port 125 constituting the electrophoretic-medium-injection mechanism.

The specimen-injection mechanism includes the syringe 123 provided corresponding to a position of the specimen reservoir 15$s$ when the chip 1 is positioned at the position B, a moving mechanism (not shown) for moving the syringe 123 in a three-dimensional direction (see an arrow 127 in the figure), and a cylinder driving mechanism (not shown) for permitting the syringe 123 to be engaged in suction and discharging. The suction/discharge opening of the syringe 123 is permitted to advance into the specimen reservoir 15$s$ by the moving mechanism constituting the specimen-injection mechanism when the chip 1 is at the position B.

The port 125 is connected to a syringe (not shown) for containing an electrophoretic medium and is provided with a nozzle 131 given corresponding to a position of the anode reservoir 15$a$ when the chip 1 is positioned at the position B. At the tip of the nozzle 131 is provided a seal member 133. The electrophoretic-medium injecting mechanism is comprised of the port 125, a syringe for pushing out an electrophoretic medium of the nozzle 131, and an elevation mechanism (not shown) for lifting/lowering the port 125 in a direction indicated by an arrow 135 in the figure. The elevation mechanism lowers the port 125 when the chip 1 is at the position B, thus bringing the top of the nozzle 131 in contact with the anode port 15$a$ through the seal member 133.

Above the position C is provided an electrode port 137. The port 137 is provided with an electrode fixing member 139 and four electrodes 141 fixed to the member 139 corresponding to an arrangement of the reservoirs 15$a$, 15$c$, 15$s$, and 15$w$ when the chip 1 is positioned at the position C. The electrodes 141 are connected to the high-voltage supplying device (not shown). Furthermore, the port 137 is provided with an elevation mechanism (not shown) for lifting/lowering the member 139, lifting/lowering the member 115 in a direction indicated by an arrow 143 in the figure. The electrode port 137, the high-voltage supplying device, and the elevation mechanism constitute the voltage supplying mechanism. This elevation mechanism lowers the member 139 so that the tips of the electrodes 141 may advance into the reservoirs 15$a$, 15$c$, 15$s$, and 15$w$ respectively when the chip 1 is at the position C.

Below the position C is provided a detecting optical system (detecting mechanism) 145. The detecting optical system 145 applies a detection light 147 to a detection position along the separation passage 13 between an intersection and the anode reservoir 15$a$ when the chip 1 is at the position C to thereby detect a separated specimen based on a ultraviolet absorbance amount.

The chip holding mechanism, the electrophoretic-medium suction-and-buffer-liquid injection port 113, the specimen injection mechanism, and the electrophoretic-medium injection mechanism, the voltage supplying mechanism, and the detecting optical system 145 are controlled by the control part (not shown).

FIG. 12 is a flowchart for showing an example of operations of this embodiment. Those operations of this embodiment shall be described with reference to FIGS. 11 and 12. Here, the electrophoretic medium to be employed contains an organic polymer (hereinafter abbreviated as polymer).

The chip 1 is positioned at the position B (step S1).

The electrophoretic-medium loading port 125 is lowered to permit the tip of the nozzle 131 to come in contact with the anode reservoir 15$a$ of the chip 1 through the seal member 133. A polymer contained in the syringe is pushed out of it and injected under pressure through the nozzle 131 and the anode reservoir 15$a$ into the channel and the reservoirs 15$c$, 15$s$, and 15$w$ of the chip 1. When the polymer comes out from all of the reservoirs 15$c$, 15$s$, and 15$w$, the injection is ended (step S2).

The electrophoretic-medium loading port 125 is lifted back to move the chip 1 to the position A (step S3).

The electrophoretic-medium suction-and-buffer liquid injection port 113 is lowered to permit the nozzles 117 and 119 to advance into the polymer contained in the reservoirs 15$a$, 15$c$, 15$s$, and 15$w$. The sucking mechanism linked to the suction nozzle 117 operates to suck through the suction nozzle 117 the polymer contained in the reservoirs 15$a$, 15$c$, 15$s$, and 15$w$ (step S4). After the removal of the polymer, the discharge mechanism linked to the discharge nozzle 119 corresponding to the reservoirs 15$c$, 15$s$, and 15$w$ operates to inject a buffer liquid through the discharge nozzle 119 into the reservoirs 15$c$, 15$s$, and 15$w$ except the specimen reservoir 15$s$ (step S5).

The port 113 is lifted back to move the chip 1 to the position B (step S6).

The syringe 123 moves to permit the suction/discharge opening of the syringe 123 to advance into the empty specimen reservoir 15$s$. The syringe 123 starts suction to inject into the specimen reservoir 15s the specimen sucked into the syringe 123 from a specimen port (not shown) beforehand (step S7).

The syringe 123 is lifted back to move the chip 1 to the position C (step S8).

The electrode port 137 is lowered to permit the electrodes 141 to come in contact with the buffer liquid or the specimen contained in the reservoirs 15a, 15c, 15s, and 15w. A predetermined voltage is applied via the electrodes 141 on the buffer liquid or the specimen contained in the reservoirs 15a, 15c, 15s, and 15w to thereby guide the specimen to the intersection between the specimen-introduction passage and the separation passage and then switch the voltage, thus injecting the specimen into the separation passage (step S9).

The port 137 is lifted back to move the chip 1 to the position A (step S10).

The port 113 is lowered to permit the nozzles 117 and 119 to advance into the specimen or the buffer liquid contained in the reservoirs 15a, 15c, 15s, and 15w. The sucking mechanism linked to the suction nozzle 117 corresponding to the specimen reservoir 15s operates to suck and remove an extra specimen left in the specimen reservoir 15s through the suction nozzle 117 (step S11). After the removal of the specimen, the discharge mechanism linked to the discharge nozzle 119 corresponding to the specimen reservoir 15s operates to inject the buffer liquid into the specimen reservoir 15s through the discharge nozzle 119 (step S12).

The port 113 is lifted back to move the chip 1 to the position C (step S13).

The electrode port 137 is lowered to permit the electrodes 141 to come in contact with the buffer liquid contained in the reservoirs 15a, 15c, 15s, and 15w. A predetermined voltage is applied through the electrodes 141 on the reservoirs 15a, 15c, 15s, and 15w to electrophoretically separate the specimen injected in the separation passage, thus detecting the separated specimen using the detecting optical system 145 (step S14).

Thus, in the embodiment of FIG. 11, it is possible to automatically perform all of the polymer injection into the electrophoretic chip, the removal of the polymer from the reservoirs, the injection of the specimen and buffer liquid into the reservoirs, the removal of the specimen from the reservoirs after it is injected into the separation passage, the injection of the buffer liquid into the reservoirs after the removal of the specimen, and the separation and detection of the specimen.

FIG. 13 is a flowchart for showing another example of the operations of this embodiment. The operation of this embodiment shall be described below with reference to FIGS. 11 and 13. Here, as the electrophoretic medium was used an inorganic ionic buffer (hereinafter called electrophoretic buffer).

The chip 1 is positioned at the position B (step S21).

The electrophoretic-medium loading port 125 is lowered to permit the tip of the nozzle 131 to come in contact with the anode reservoir 15a of the chip 1 through the seal member 133. The channels and the reservoirs 15c, 15s, and 15w of the chip 1 are filled with an electrophoretic buffer through the nozzle 131 and the anode reservoir 15a from the syringe containing the electrophoretic buffer. When the electrophoretic buffer comes out from all of the reservoirs 15c, 15s, and 15w, the filling is ended (step S22). Although in this case the electrophoretic buffer is injected from the electrophoretic-medium loading port 125, the chip 1 may be moved to the position A to use the electrophoretic-medium suction and buffer liquid injection port 113, the discharge nozzle 119 and the discharge mechanism linked to the discharge nozzle 119, thus filling the electrophoretic buffer.

After the electrophoretic-medium loading port 125 is lifted back the syringe 123 moves to permit the suction/discharge opening of the syringe 123 to advance to the vicinity of the inlet of the specimen-introduction passage in the specimen reservoir 15s. The syringe 123 starts suction to thereby inject into the specimen reservoir 15s the specimen sucked beforehand in the syringe 123 from a specimen port (not shown) (step S23).

The syringe 123 is lifted back to move the chip 1 to the position C (step s24).

The electrode port 137 is lowered to permit the electrodes 141 to come in contact with the electrophoretic buffer or specimen contained in the reservoirs 15a, 15c, 15s, and 15w. A predetermined voltage is applied through the electrodes 141 on the electrophoretic buffer or specimen contained in the reservoirs 15a, 15c, 15s, and 15w to guide the specimen to the intersection between the specimen-introduction passage and the separation passage and then switch the voltage in order to inject the specimen into the separation passage (step S25) and, subsequently, electrophoretically separate the specimen so that the separated specimen can be detected by the detecting optical system 145 (step S26).

Thus, it is possible in this embodiment to perform all the injection of the electrophoretic buffer into the electrophoretic chip, the injection of the specimen into the reservoirs, and the separation and detection of the specimen.

In this case, the channels of the chip 1 can be designed arbitrarily.

The electrophoretic medium employed here is not particularly restrictive, and it may be any electrophoretic medium such as an electrophoretic buffer of an inorganic ionic buffer such as tris-boric acid, or one contains an organic polymer such as hydroxy-methyl cellulose, hydroxy-ethyl cellulose or poly acryl-amide.

Furthermore, the electrophoretic buffer and the buffer liquid are not particularly restrictive, tris-boric acid-EDTA (ethylene diamine tetra-acetic acid) (TBE) based or tris-TAPS (tetrapentylammonium 3-[tris(hydroxymethyl)methylamino]-1-propanesulfate)-EDTA (TTE) based ones may be used according to the electrophoretic medium or the measurement conditions employed.

Although in the embodiment shown in FIG. 11 a syringe is used as the sucking mechanism connected to the suction nozzle 117, the invention is not limited to it for example, any other sucking mechanism such as a vacuum pump, an aspirator or the like may be used instead.

Also, although the suction nozzles 117 are connected to the respective independent syringes, the invention is not limited to it, as far as at least the suction nozzle 117 for the specimen reservoir 15s is connected to the independent syringe, the suction nozzles 117 for the other reservoirs 15a, 15b, and 15w may be connected to the common syringe. This holds true also in a case where any other sucking mechanism is used in place of the syringe.

Although a syringe is used as the discharge mechanism connected to the discharge nozzle 119, the invention is not limited to it; for example, any other discharge mechanism such as a perister pump or a pressure-application mechanism by use of air may be used.

Also, although the discharge nozzles 119 are connected to the respective independent syringes, the invention is not limited to it; for example, as far as at least the discharge nozzle 119 for the specimen reservoir 15s is connected to an independent syringe, the discharge nozzles 119 for the other reservoirs 15a, 15b, and 15w may be connected to the common syringe. This holds true also with a case where any other discharge mechanism is used in place of the syringe.

Although in the above-mentioned embodiment a syringe is provided for each of the suction nozzles 117 and for the discharge nozzle 119, the invention is not limited to it, one common syringe and a switching valve for switching it between the suction nozzle 117 and the discharge nozzle 119 in connection may be provided, to utilize the switching of the switching valve and the operations of the syringe, thus effectuating suction from the suction nozzle 117 and discharge from the discharge nozzle 119. This holds true also in a case where the syringe is replaced by any other suction/discharge mechanism.

Although in the embodiment shown in FIG. 11 the detecting mechanism employed detects a separated specimen using an ultraviolet absorbing method, the invention is not limited to it, and such a detecting mechanism may be used that utilizes any other detecting principle such as detection by use of one color or a plurality of colors of fluorescent lights or detection based on scattering of an applied detection light. Also, although the detecting mechanism employed detects a specimen at a one-point detection position, the invention is not limited to it; for example, such a mechanism may be used that detects an image within a predetermined range along the separation passage.

Although in the embodiment of FIG. 11 the electrophoretic chip migrates between the positions A, B, and C, the invention is not limited to it; for example, the electrophoretic chip may be fixed to the chip holding station so that the electrophoretic-medium filling mechanism, the electrophoretic-medium sucking mechanism, the buffer-liquid injection mechanism, the specimen injection mechanism, the specimen sucking mechanism, and the voltage supplying mechanism or a combination thereof may be moved above or below the fixed electrophoretic chip.

Although in the embodiment of FIG. 11 the electrophoretic chip provided with the four reservoirs is used, the invention is not limited to it; for example, the invention may be applied to such an electrophoretic chip that is provided with at least five reservoirs, that is, many separation passages.

Furthermore, although in the embodiment of FIG. 11 the electrophoretic chip having the mutually intersecting specimen-introduction passages and separation passages formed therein, the invention is not limited to it; for example, the invention may be applied to such an electrophoretic chip that has formed therein separation passage intersecting with no passage, that has formed therein a separation passage intersecting with a plurality of passages, that has multiple channels, or that has a large size. In such a case, it is necessary to change the nozzle configuration of the electrophoretic-medium filling mechanism, the electrophoretic-medium sucking mechanism, the buffer-liquid injection mechanism, the specimen-injection mechanism, and the specimen sucking mechanism according to the arrangement of the reservoirs.

Although in FIG. 11 such a voltage supplying mechanism is provided that is equipped with the electrodes 141 permitted to advance into the buffer liquid and the specimen, the invention is not limited to it; for example, such a voltage supplying mechanism may be used that is equipped with electrodes for connection to chip side electrodes, if formed on the surface of the electrophoretic chip, for continuity to the reservoirs.

The electrophoretic apparatus shown in FIG. 11 is provided with the chip holding mechanism, the electrophoretic-medium filling mechanism, the specimen injection mechanism, the voltage supplying mechanism, the detecting mechanism, and the control part for controlling these mechanisms so as to operate these mechanisms, thus enabling automatically filling the chip device with an electrophoretic medium, injecting the specimen into one of the reservoirs, and separating and detecting the specimen.

If it further includes the electrophoretic sucking mechanism for removing the electrophoretic medium contained in the reservoirs and the buffer-liquid injection mechanism for injecting the buffer liquid into the reservoirs after the electrophoretic medium is removed therefrom in such a configuration that the control part controls the electrophoretic-medium sucking mechanism and the buffer-liquid injection mechanism so that they may operate automatically in such a manner that the electrophoretic sucking mechanism would remove the electrophoretic medium from the reservoirs and, into the reservoirs from which the electrophoretic medium is thus removed, the buffer-liquid injection mechanism would inject the buffer liquid, even in a case where such an electrophoretic medium is used that cannot come in direct contact with the electrode for voltage application, and a voltage can be applied on the electrophoretic medium through the buffer liquid.

Furthermore, by providing the specimen injection mechanism, the electrophoretic-medium sucking mechanism, and the buffer-liquid injection mechanism independently of each other, a process of cleaning the nozzles, for example, can be omitted to thereby greatly reduce the analysis cycle time, thus resulting in a higher throughput.

Furthermore, the reservoirs can be filled with a buffer liquid simultaneously, thus mitigating the influence of a head difference (water head difference).

It is possible to prevent an excessive amount of the specimen from being injected into the passages if a specimen sucking mechanism for removing the specimen left in the reservoirs is further provided and also controlled by the control part so as to operate automatically in such a manner that after a specimen is injected into the passage when a voltage is applied by the voltage supplying part on the reservoirs the voltage application is once stopped to operate the specimen sucking mechanism to remove, by suction, the specimen left in the specimen reservoir and then the voltage application is restarted on the reservoirs to separate and detect the specimen.

Furthermore, the specimen injection mechanism and the specimen sucking mechanism are provided independently of each other and the nozzle cleaning process can be omitted to thereby greatly reduce the analysis cycle time, thus resulting in a higher throughput.

What is claimed is:

1. An electrophoretic apparatus comprising:
an electrophoretic member in which a plate-shaped member thereof has one or a plurality of passages formed therein and also such holes reaching the passage that are formed at positions corresponding to both ends of the passage on one surface of the plate-shaped member, each of the passages comprising a specimen-injection-passage and a separation-passage which intersect with each other;
a voltage applying part for applying a voltage across the passage;
a detecting part for detecting a specimen present in the separation passage; and a specimen-injection monitor mechanism provided with CCD for detecting a specimen at a site where a specimen is injected into the specimen-injection-passage, the specimen-injection monitor mechanism being installed separately from the detecting part, wherein the specimen-injection monitor mechanism detects a specimen distribution along the specimen-injection-passage including at least the intersection between the specimen-injection-passage and the separation-passage, wherein the detecting part comprises a fluorescent-light detecting device for detecting a fluorescent light in a detection range, the fluorescent-light detecting device comprising:

a first optical system for focusing, for image formation, a light from the detecting range into a slit hole; and a second optical system provided with a reflection-type diffraction grating, for separating a light from the slit hole and focusing the light, for image formation, onto a detecting element, wherein the specimen-injection monitor mechanism and the detecting mechanism are each provided with a fluorescent-light detecting optical system, which shares a common excitation light source in use.

2. The electrophoretic apparatus according to claim 1, wherein:

the apparatus further comprises a control part which (a) causes the voltage applying part to supply a voltage for guiding a specimen to an intersection between the specimen injection passage and the separation passage, and (b) stops the voltage application to the passages upon the specimen-injection monitor mechanism detecting a non-uniform specimen distribution in a predetermined area after a predetermined time has elapsed.

3. The electrophoretic apparatus according to claim 1, wherein:

the apparatus further comprises a control part which stops voltage application to said passages upon the specimen-injection monitor mechanism detecting a specimen present at said intersection as a result of the voltage applying part failing to electrophoretically migrate the specimen into the separation passage.

4. An electrophoretic apparatus comprising:

an electrophoretic member in which a plate-shaped member thereof has one or a plurality of passages formed therein and also such holes reaching the passage that are formed at positions corresponding to both ends of the passage on one surface of the plate-shaped member, each of the passages comprising a specimen-injection-passage and a separation-passage which intersect with each other;

a voltage applying part for applying a voltage across the passage;

a detecting part for detecting a specimen present in the separation-passage; and a specimen-injection monitor mechanism provided with CCD for detecting a specimen at a site where a specimen is injected into the specimen-injection-passage, the specimen-injection monitor mechanism being installed separately from the detecting part, wherein the specimen-injection monitor mechanism detects a specimen distribution along the specimen-injection-passage including at least the intersection between the specimen-injection-passage and the separation-passage, wherein the detecting part comprises a fluorescent-light detecting device for detecting a fluorescent light in a detection range, the fluorescent-light detecting device comprising:

a first optical system for focusing, for image formation, a light from the detecting range into a slit hole; and a second optical system provided with a reflection-type diffraction grating, for separating a light from the slit hole and focusing the light, for image formation, onto a detecting element, wherein the specimen-injection monitor mechanism is provided with a detecting optical system having an LED as a light source thereof.

5. The electrophoretic apparatus according to claim 4, wherein:

the apparatus further comprises a control part which (a) causes the voltage applying part to supply a voltage for guiding a specimen to an intersection between the specimen injection passage and the separation passage, and (b) stops the voltage application to the passages upon the specimen-injection monitor mechanism detecting a non-uniform specimen distribution in a predetermined area after a predetermined time has elapsed.

6. The electrophoretic apparatus according to claim 4, wherein: the apparatus further comprises a control part which stops voltage application to said passages upon the specimen-injection monitor mechanism detecting a specimen present at said intersection as a result of the voltage applying part failing to electrophoretically migrate the specimen into the separation passage.

* * * * *